US012629838B2

(12) United States Patent
Simi et al.

(10) Patent No.: US 12,629,838 B2
(45) Date of Patent: May 19, 2026

(54) METHOD FOR DETECTING OPERATING ANOMALIES OF AN UNCONSTRAINED MASTER DEVICE OF A MASTER-SLAVE ROBOTIC SYSTEM FOR MEDICAL OR SURGICAL TELEOPERATION AND RELATED ROBOTIC SYSTEM

(71) Applicant: MEDICAL MICROINSTRUMENTS, INC., Wilmington, DE (US)

(72) Inventors: Massimiliano Simi, Pisa (IT); Matteo Tanzini, Pisa (IT); Emanuele Ruffaldi, Pisa (IT); Matteo Bagheri Ghavifekr, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 36 days.

(21) Appl. No.: 18/546,193

(22) PCT Filed: Feb. 15, 2022

(86) PCT No.: PCT/IB2022/051321
§ 371 (c)(1),
(2) Date: Aug. 11, 2023

(87) PCT Pub. No.: WO2022/175807
PCT Pub. Date: Aug. 25, 2022

(65) Prior Publication Data
US 2024/0131714 A1 Apr. 25, 2024
US 2024/0227192 A9 Jul. 11, 2024

(30) Foreign Application Priority Data
Feb. 16, 2021 (IT) ........................ 102021000003422

(51) Int. Cl.
B25J 9/16 (2006.01)
A61B 34/00 (2016.01)
(Continued)

(52) U.S. Cl.
CPC ............. *B25J 9/1689* (2013.01); *A61B 34/20* (2016.02); *A61B 34/35* (2016.02); *A61B 34/77* (2016.02)

(58) Field of Classification Search
CPC ........ B25J 9/1689; B25J 9/1674; B25J 19/02; B25J 3/02; B25J 9/1676; A61B 34/20; (Continued)

(56) References Cited

U.S. PATENT DOCUMENTS 6,063,095 A 5/2000 Wang
6,364,888 B1 4/2002 Niemeyer
(Continued)

FOREIGN PATENT DOCUMENTS

DE 102010009065 A1 8/2011
DE 102014006264 A1 11/2015
(Continued)

OTHER PUBLICATIONS

International Search Report and Written Opinion received for PCT Serial No. PCT/IB2022/051226 on Apr. 8, 2022, 15 pgs.
(Continued)

*Primary Examiner* — Bao Long T Nguyen
(74) *Attorney, Agent, or Firm* — Merchant & Gould P.C.

(57) ABSTRACT

A method is for identifying at least one anomaly condition in using a hand-held, mechanically unconstrained master device to control a robotic system for medical or surgical teleoperation. The method includes detecting, by sensor(s), the position vector of a point belonging to or integral with the master device, or of a virtual point uniquely and rigidly associated with the master device. A detectable anomaly is identified based on the detected position vector, or based on a component of the detected position vector. The detectable anomalies include at least an incorrect positioning of the master device with respect to a predetermined workspace of
(Continued)

the master device. Each of such detectable anomalies is associated with a system state change to be performed if the anomaly is detected, in which the state change includes exiting from the teleoperation state. A robotic system for medical or surgical teleoperation performs the method.

18 Claims, 10 Drawing Sheets

(51) Int. Cl.
 *A61B 34/20* (2016.01)
 *A61B 34/35* (2016.01)
(58) Field of Classification Search
 CPC ................... A61B 34/35; A61B 34/77; A61B 2017/00207; A61B 2017/00212; A61B 2034/2046; A61B 2034/741; A61B 2090/067; A61B 34/37; A61B 34/74; A61B 90/06; A61B 2090/0801; A61B 2560/0276; A61B 2034/2048; A61B 2017/00119; A61B 90/03; A61B 34/30; G05B 2219/40164
 See application file for complete search history.

(56) References Cited

U.S. PATENT DOCUMENTS

| | | | |
|---|---|---|---|
| 6,424,885 B1 | 7/2002 | Niemeyer |
| 6,459,926 B1 | 10/2002 | Nowlin |
| 6,594,552 B1 | 7/2003 | Nowlin |
| 6,671,581 B2 | 12/2003 | Niemeyer |
| 6,766,204 B2 | 7/2004 | Niemeyer |
| 6,879,880 B2 | 4/2005 | Nowlin |
| 7,087,049 B2 | 8/2006 | Nowlin |
| 7,155,315 B2 | 12/2006 | Niemeyer |
| 7,331,967 B2 | 2/2008 | Lee |
| 7,373,219 B2 | 5/2008 | Nowlin |
| 7,778,733 B2 | 8/2010 | Nowlin |
| 7,806,891 B2 | 10/2010 | Nowlin |
| 7,886,743 B2 | 2/2011 | Cooper |
| 7,947,050 B2 | 5/2011 | Lee |
| 7,967,137 B2 | 6/2011 | Fulbrook |
| 8,004,229 B2 | 8/2011 | Nowlin |
| 8,005,571 B2 | 8/2011 | Sutherland |
| 8,123,740 B2 | 2/2012 | Madhani |
| 8,220,468 B2 | 7/2012 | Cooper |
| 8,281,670 B2 | 10/2012 | Larkin |
| 8,368,649 B2 | 2/2013 | Hall |
| 8,375,808 B2 | 2/2013 | Blumenkranz |
| 8,521,331 B2 | 8/2013 | Itkowitz |
| 8,540,748 B2 | 9/2013 | Murphy |
| 8,543,240 B2 | 9/2013 | Itkowitz |
| 8,620,473 B2 | 12/2013 | Diolaiti |
| 8,638,057 B2 | 1/2014 | Goldberg |
| 8,677,820 B2 | 3/2014 | Nakagawa |
| 8,812,160 B2 | 8/2014 | Hagn |
| 8,831,782 B2 | 9/2014 | Itkowitz |
| 8,935,003 B2 | 1/2015 | Itkowitz |
| 8,939,963 B2 | 1/2015 | Rogers |
| 8,996,173 B2 | 3/2015 | Itkowitz |
| 9,060,796 B2 | 6/2015 | Seo |
| 9,101,379 B2 | 8/2015 | Au |
| 9,333,042 B2 | 5/2016 | Diolaiti |
| 9,387,043 B2 | 7/2016 | Yang |
| 9,408,668 B2 | 8/2016 | Durant |
| 9,452,020 B2 | 9/2016 | Griffiths |
| 9,492,927 B2 | 11/2016 | Diolaiti |
| 9,554,866 B2 | 1/2017 | Cunningham |
| 9,629,680 B2 | 4/2017 | Winer |
| 9,632,573 B2 | 4/2017 | Ogawa |
| 9,707,684 B2 | 7/2017 | Ruiz Morales |
| 9,743,989 B2 | 8/2017 | Itkowitz |
| 9,770,300 B2 | 9/2017 | Kwon |
| 9,855,662 B2 | 1/2018 | Ruiz Morales |
| 9,901,402 B2 | 2/2018 | Itkowitz |
| 9,949,799 B2 | 4/2018 | Hingwe |
| 9,968,405 B2 | 5/2018 | Cooper |
| 10,013,082 B2 | 7/2018 | Schecter |
| 10,034,718 B2 | 7/2018 | Griffiths |
| 10,052,164 B2 | 8/2018 | Overmyer |
| 10,085,810 B2 | 10/2018 | Vakharia |
| 10,123,844 B2 | 11/2018 | Nowlin |
| 10,188,472 B2 | 1/2019 | Diolaiti |
| 10,219,870 B2 | 3/2019 | Mondry |
| 10,219,898 B2 | 3/2019 | Forsell |
| 10,271,915 B2 | 4/2019 | Diolaiti |
| 10,292,661 B1 | 5/2019 | LaBorde |
| 10,299,873 B2 | 5/2019 | Hares |
| 10,299,883 B2 | 5/2019 | Kilroy |
| 10,307,199 B2 | 6/2019 | Farritor |
| 10,321,964 B2 | 6/2019 | Grover |
| 10,357,320 B2 | 7/2019 | Beira |
| 10,357,324 B2 | 7/2019 | Flatt |
| 10,376,323 B2 | 8/2019 | Farritor |
| 10,376,337 B2 | 8/2019 | Kilroy |
| 10,383,699 B2 | 8/2019 | Kilroy |
| 10,393,109 B2 | 8/2019 | Wu |
| 10,413,374 B2 | 9/2019 | Chassot |
| 10,420,618 B2 | 9/2019 | Grover |
| 10,470,830 B2 | 11/2019 | Hill |
| 10,485,621 B2 | 11/2019 | Morrissette |
| 10,512,514 B2 | 12/2019 | Nowlin |
| 10,512,515 B2 | 12/2019 | Bailey |
| 10,524,871 B2 | 1/2020 | Liao |
| 10,531,929 B2 | 1/2020 | Widenhouse |
| 10,543,050 B2 | 1/2020 | Itkowitz |
| 10,561,468 B2 | 2/2020 | Cunningham |
| 10,568,703 B2 | 2/2020 | Nobles |
| 10,568,704 B2 | 2/2020 | Savall |
| 10,603,123 B2 | 3/2020 | Vakharia |
| 10,617,484 B2 | 4/2020 | Kilroy |
| 10,624,708 B2 | 4/2020 | Hunter |
| 10,639,114 B2 | 5/2020 | Schuh |
| 10,653,489 B2 | 5/2020 | Kopp |
| 10,661,453 B2 | 5/2020 | Koenig |
| 10,736,701 B2 | 8/2020 | Savall |
| 10,736,706 B2 | 8/2020 | Scheib |
| 10,751,136 B2 | 8/2020 | Farritor |
| 10,758,298 B2 | 9/2020 | Felder |
| 10,779,898 B2 | 9/2020 | Hill |
| 10,786,327 B2 | 9/2020 | Anderson |
| 10,789,329 B2 | 9/2020 | Lanting |
| 10,813,713 B2 | 10/2020 | Koch |
| 10,820,953 B2 | 11/2020 | Kralicky |
| 10,842,577 B2 | 11/2020 | Kilroy |
| 10,842,581 B2 | 11/2020 | Bailey |
| 10,881,477 B1 | 1/2021 | Genova |
| 10,888,390 B2 | 1/2021 | Higuchi |
| 10,898,281 B2 | 1/2021 | Cooper |
| 10,912,618 B2 | 2/2021 | Vakharia |
| 10,959,798 B2 | 3/2021 | Diolaiti |
| 10,987,192 B2 | 4/2021 | Garcia Kilroy |
| 11,037,464 B2 | 6/2021 | Ho |
| 11,045,268 B2 | 6/2021 | Grover |
| 11,083,532 B2 | 8/2021 | Liao |
| 11,083,534 B2 | 8/2021 | Hares |
| 11,096,746 B2 | 8/2021 | Savall |
| 11,109,925 B2 | 9/2021 | Cooper |
| 11,135,031 B2 | 10/2021 | Savall |
| 11,172,997 B2 | 11/2021 | Kostrzewski |
| 11,179,209 B2 | 11/2021 | Kralicky |
| 11,179,211 B2 | 11/2021 | Zemlok |
| 11,179,213 B2 | 11/2021 | Huang |
| 11,213,364 B2 | 1/2022 | Popovic |
| 11,246,670 B2 | 2/2022 | Swayze |
| 11,266,469 B2 | 3/2022 | Fuerst |
| 11,284,957 B2 | 3/2022 | Denlinger |
| 11,284,959 B2 | 3/2022 | Bailey |
| 11,344,374 B2 | 5/2022 | Tekiela |
| 11,357,597 B2 | 6/2022 | Jhaveri |
| 11,399,908 B2 | 8/2022 | Diolaiti |
| 11,406,465 B2 | 8/2022 | Zemlok |

(56) References Cited

U.S. PATENT DOCUMENTS

| | | |
|---|---|---|
| 11,439,478 B2 | 9/2022 | Anderson |
| 11,446,097 B2 | 9/2022 | Savall |
| 11,457,987 B2 | 10/2022 | He |
| 11,478,318 B2 | 10/2022 | Cone |
| 11,478,928 B2 | 10/2022 | Hariri |
| 11,484,379 B2 | 11/2022 | Sutherland |
| 11,504,197 B1 | 11/2022 | Noonan |
| 11,504,203 B2 | 11/2022 | Flatt |
| 11,534,246 B2 | 12/2022 | Fuerst |
| 11,534,252 B2 | 12/2022 | DiMaio |
| 11,576,733 B2 | 2/2023 | Anglese |
| 11,607,279 B2 | 3/2023 | Chaplin |
| 11,666,401 B2 | 6/2023 | Denlinger |
| 11,684,434 B2 | 6/2023 | Shelton |
| 11,707,336 B2 | 7/2023 | Itkowitz |
| 11,712,314 B2 | 8/2023 | Thompson |
| 12,048,505 B2 | 7/2024 | Thompson |
| 2002/0055795 A1 | 5/2002 | Niemeyer |
| 2002/0128552 A1 | 9/2002 | Nowlin et al. |
| 2003/0004610 A1 | 1/2003 | Niemeyer |
| 2003/0195664 A1 | 10/2003 | Nowlin |
| 2004/0039485 A1 | 2/2004 | Niemeyer |
| 2005/0194507 A1 | 9/2005 | White |
| 2006/0030840 A1 | 2/2006 | Nowlin |
| 2006/0106493 A1 | 5/2006 | Niemeyer |
| 2006/0241414 A1 | 10/2006 | Nowlin |
| 2008/0114494 A1 | 5/2008 | Nixon |
| 2008/0154246 A1 | 6/2008 | Nowlin |
| 2009/0301927 A1 | 12/2009 | Fulbrook |
| 2010/0053085 A1 | 3/2010 | Hall |
| 2010/0094312 A1 | 4/2010 | Ruiz Morales |
| 2010/0274087 A1 | 10/2010 | Diolaiti |
| 2011/0118748 A1 | 5/2011 | Itkowitz |
| 2012/0011932 A1 | 1/2012 | Nakagawa |
| 2012/0059391 A1 | 3/2012 | Diolaiti |
| 2012/0071891 A1 | 3/2012 | Itkowitz |
| 2012/0071892 A1 | 3/2012 | Itkowitz |
| 2012/0316681 A1 | 12/2012 | Hagn |
| 2013/0012930 A1 | 1/2013 | Ruiz Morales |
| 2013/0035697 A1* | 2/2013 | Ogawa .................. A61B 34/37 606/130 |
| 2013/0316681 A1 | 11/2013 | Huang |
| 2013/0321262 A1 | 12/2013 | Schecter |
| 2014/0018960 A1 | 1/2014 | Itkowitz |
| 2014/0160015 A1 | 6/2014 | Ogawa |
| 2014/0171964 A1 | 6/2014 | Yang |
| 2014/0222021 A1 | 8/2014 | Diolaiti |
| 2015/0025549 A1 | 1/2015 | Kilroy |
| 2015/0038981 A1 | 2/2015 | Kilroy |
| 2015/0038982 A1 | 2/2015 | Kilroy |
| 2015/0066051 A1 | 3/2015 | Kwon |
| 2015/0080909 A1 | 3/2015 | Itkowitz |
| 2015/0157410 A1 | 6/2015 | Kilroy |
| 2015/0182289 A1 | 7/2015 | Itkowitz |
| 2016/0242860 A1 | 8/2016 | Diolaiti |
| 2016/0287279 A1 | 10/2016 | Bovay |
| 2017/0035521 A1 | 2/2017 | Diolaiti |
| 2017/0095295 A1 | 4/2017 | Overmyer |
| 2017/0095298 A1 | 4/2017 | Vakharia |
| 2017/0156806 A1 | 6/2017 | Prisco |
| 2017/0224428 A1 | 8/2017 | Kopp |
| 2017/0252112 A1 | 9/2017 | Crawford |
| 2017/0265949 A1 | 9/2017 | Crawford |
| 2017/0312043 A1 | 11/2017 | Ogawa |
| 2017/0319284 A1 | 11/2017 | Itkowitz |
| 2018/0025666 A1 | 1/2018 | Ho |
| 2018/0036088 A1 | 2/2018 | Kilroy |
| 2018/0078034 A1 | 3/2018 | Savall |
| 2018/0078319 A1 | 3/2018 | Nobles |
| 2018/0078321 A1 | 3/2018 | Liao |
| 2018/0092706 A1* | 4/2018 | Anderson .............. A61B 90/50 |
| 2018/0161108 A1 | 6/2018 | Savall |
| 2018/0168681 A1 | 6/2018 | Kirk |
| 2018/0168759 A1 | 6/2018 | Kilroy |
| 2018/0194013 A1 | 7/2018 | Ruiz Morales |
| 2018/0214223 A1 | 8/2018 | Turner |
| 2018/0235719 A1 | 8/2018 | Jarc |
| 2019/0012006 A1 | 1/2019 | Schecter |
| 2019/0029770 A1 | 1/2019 | Bailey |
| 2019/0069960 A1 | 3/2019 | Vakharia |
| 2019/0110847 A1 | 4/2019 | Diolaiti |
| 2019/0142530 A1 | 5/2019 | Thompson |
| 2019/0201152 A1 | 7/2019 | Diolaiti |
| 2019/0239972 A1 | 8/2019 | Chassot |
| 2019/0307524 A1 | 10/2019 | Popovic |
| 2019/0314097 A1 | 10/2019 | Diolaiti |
| 2019/0343594 A1 | 11/2019 | Garcia Kilroy |
| 2019/0380791 A1* | 12/2019 | Fuerst .................... A61B 34/25 |
| 2019/0380802 A1 | 12/2019 | Savall |
| 2019/0380809 A1 | 12/2019 | Fuerst |
| 2020/0008901 A1 | 1/2020 | Garcia Kilroy |
| 2020/0015918 A1 | 1/2020 | Payyavula |
| 2020/0022775 A1 | 1/2020 | Garcia Kilroy |
| 2020/0046439 A1* | 2/2020 | Tekiela .................. A61B 34/74 |
| 2020/0046450 A1 | 2/2020 | Tsao |
| 2020/0069388 A1 | 3/2020 | Bailey |
| 2020/0085522 A1 | 3/2020 | Liao |
| 2020/0113641 A1 | 4/2020 | Itkowitz |
| 2020/0138534 A1 | 5/2020 | Garcia Kilroy |
| 2020/0179068 A1 | 6/2020 | Peine |
| 2020/0194117 A1 | 6/2020 | Krieger |
| 2020/0197112 A1 | 6/2020 | Chin |
| 2020/0197115 A1 | 6/2020 | Vakharia |
| 2020/0205922 A1 | 7/2020 | Cone |
| 2020/0214773 A1 | 7/2020 | Nobles |
| 2020/0214778 A1 | 7/2020 | Turner |
| 2020/0214779 A1 | 7/2020 | Masuda |
| 2020/0222124 A1 | 7/2020 | Savall |
| 2020/0222134 A1 | 7/2020 | Schuh |
| 2020/0275985 A1 | 9/2020 | Thompson |
| 2020/0289212 A1 | 9/2020 | Savall |
| 2020/0289223 A1 | 9/2020 | Denlinger |
| 2020/0330170 A1 | 10/2020 | Farritor |
| 2020/0360096 A1 | 11/2020 | Savall |
| 2020/0360097 A1 | 11/2020 | DiMaio |
| 2020/0390510 A1 | 12/2020 | Thompson |
| 2020/0397517 A1 | 12/2020 | Unsworth |
| 2020/0397529 A1 | 12/2020 | Anderson |
| 2020/0405408 A1 | 12/2020 | Shelton |
| 2020/0405434 A1 | 12/2020 | Schuh |
| 2021/0030495 A1* | 2/2021 | Savall .................... A61B 34/20 |
| 2021/0052338 A1 | 2/2021 | Hill |
| 2021/0052341 A1 | 2/2021 | Bailey |
| 2021/0059781 A1 | 3/2021 | Peine |
| 2021/0085301 A1 | 3/2021 | Au |
| 2021/0121260 A1 | 4/2021 | Genova |
| 2021/0153964 A1 | 5/2021 | Diolaiti |
| 2021/0153965 A1 | 5/2021 | Lau |
| 2021/0153966 A1 | 5/2021 | Lau |
| 2021/0196411 A1 | 7/2021 | Vakharia |
| 2021/0196413 A1 | 7/2021 | Inoue |
| 2021/0197401 A1 | 7/2021 | Weintraub |
| 2021/0236220 A1 | 8/2021 | Diolaiti |
| 2021/0290326 A1 | 9/2021 | Diolaiti |
| 2021/0290328 A1 | 9/2021 | Miller |
| 2021/0298855 A1 | 9/2021 | Thompson |
| 2021/0304639 A1 | 9/2021 | Ho |
| 2021/0322117 A1 | 10/2021 | Liao |
| 2021/0322119 A1 | 10/2021 | Hares |
| 2021/0353381 A1 | 11/2021 | Usui |
| 2021/0369365 A1 | 12/2021 | Goswami |
| 2022/0015839 A1 | 1/2022 | Savall |
| 2022/0015852 A1 | 1/2022 | Savall |
| 2022/0031415 A1 | 2/2022 | Vargas |
| 2022/0047345 A1 | 2/2022 | Choi |
| 2022/0096189 A1 | 3/2022 | Popovic |
| 2022/0184823 A1 | 6/2022 | Bonny |
| 2022/0192763 A1 | 6/2022 | Fuerst |
| 2022/0202437 A1 | 6/2022 | Overmyer |
| 2022/0211452 A1 | 7/2022 | Clark |
| 2022/0218418 A1 | 7/2022 | Jolaeimoghaddam |
| 2022/0226056 A1 | 7/2022 | Beckman |
| 2022/0265380 A1 | 8/2022 | Bailey |
| 2022/0361736 A1 | 11/2022 | Danna |

(56) References Cited

U.S. PATENT DOCUMENTS

| | | |
|---|---|---|
| 2022/0361970 A1 | 11/2022 | Griffiths |
| 2022/0370163 A1 | 11/2022 | Schuh |
| 2022/0378526 A1 | 12/2022 | Balicki |
| 2022/0378527 A1 | 12/2022 | Basafa |
| 2022/0378533 A1 | 12/2022 | McDiarmid |
| 2022/0387131 A1 | 12/2022 | Anderson |
| 2022/0395346 A1 | 12/2022 | Ihara |
| 2022/0401162 A1 | 12/2022 | Unsworth |
| 2023/0028689 A1 | 1/2023 | Rabindran |
| 2023/0045591 A1 | 2/2023 | de la Fuente Klein |
| 2023/0149105 A1 | 5/2023 | Thornycroft |
| 2023/0301738 A1 | 9/2023 | Thompson |
| 2023/0355261 A1 | 11/2023 | Yu |

FOREIGN PATENT DOCUMENTS

| | | |
|---|---|---|
| EP | 2845556 A1 | 3/2015 |
| EP | 3245975 A1 | 11/2017 |
| EP | 3424651 A1 | 1/2019 |
| EP | 3459429 A1 | 3/2019 |
| EP | 3574860 A1 | 12/2019 |
| EP | 3852668 | 7/2021 |
| JP | 2013034835 | 2/2013 |
| JP | 2013049121 A | 3/2013 |
| JP | 2013510671 | 3/2013 |
| JP | 2013510672 | 3/2013 |
| JP | 2016512733 A | 5/2016 |
| JP | 2016514492 A | 5/2016 |
| JP | 2017099820 | 6/2017 |
| JP | 2019536556 | 12/2019 |
| JP | 2020529237 | 10/2020 |
| JP | 2021162200 | 10/2021 |
| WO | 2013018861 A1 | 2/2013 |
| WO | 2013071071 A1 | 5/2013 |
| WO | 2014151621 A1 | 9/2014 |
| WO | 2016053657 A1 | 4/2016 |
| WO | 2016171757 A1 | 10/2016 |
| WO | 2016201207 A1 | 12/2016 |
| WO | 2017094844 A1 | 6/2017 |
| WO | 2018104252 A1 | 6/2018 |
| WO | 2018107062 A1 | 6/2018 |
| WO | 2019027922 | 2/2019 |
| WO | 2019050878 A2 | 3/2019 |
| WO | 2019099584 A1 | 5/2019 |
| WO | 2019103954 A1 | 5/2019 |
| WO | 2019220407 A1 | 5/2019 |
| WO | 2019220408 A1 | 5/2019 |
| WO | 2019220409 A1 | 5/2019 |
| WO | 20200092170 A1 | 10/2019 |
| WO | 2019240825 A1 | 12/2019 |
| WO | 2020139405 A1 | 7/2020 |
| WO | 2020153411 A1 | 7/2020 |
| WO | 2021141920 A1 | 7/2021 |
| WO | 2021188127 A1 | 9/2021 |
| WO | 2022155067 A1 | 7/2022 |

OTHER PUBLICATIONS

International Search Report and Written Opinion received for PCT Serial No. PCT/IB2022/051286 on Jun. 7, 2022, 13 pgs.
International Search Report and Written Opinion received for PCT Serial No. PCT/IB2022/051293 on Apr. 8, 2022, 16 pgs.
International Search Report and Written Opinion received for PCT Serial No. PCT/IB2022/051321 on Jun. 8, 2022, 16 pgs.
International Search Report and Written Opinion received for PCT Serial No. PCT/IB2022/051328 on Jun. 13, 2022, 16 pgs.
International Search Report and Written Opinion received for PCT Serial No. PCT/IB2022/051279 on Jun. 13, 2022, 15 pgs.
International Search Report and Written Opinion received for PCT Serial No. PCT/IB2022/051244 on Jun. 7, 2022, 13 pgs.

* cited by examiner

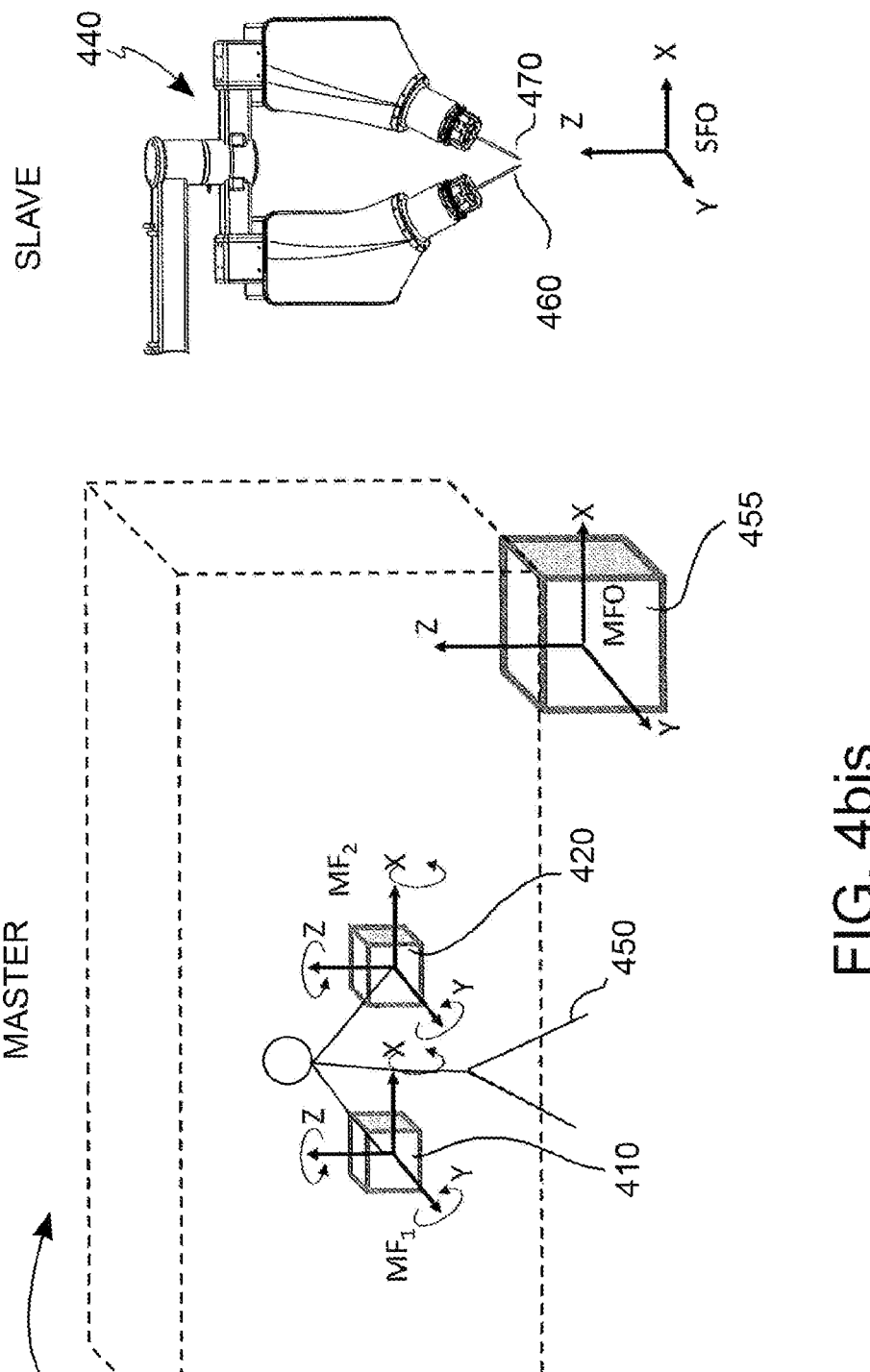
FIG. 4bis

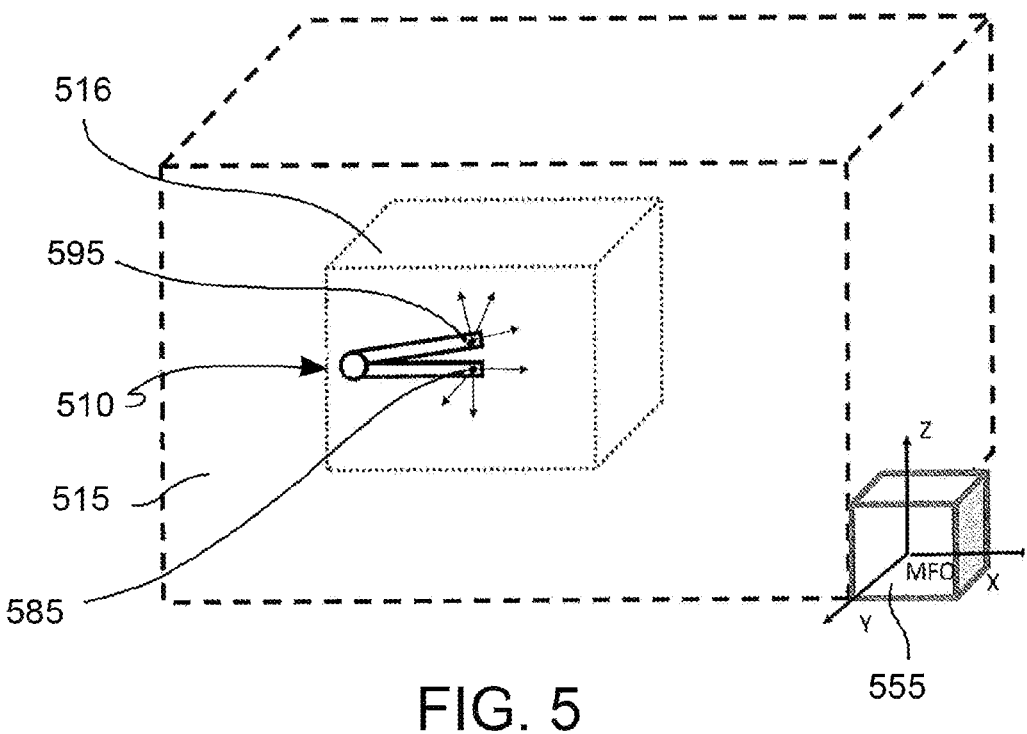
FIG. 5
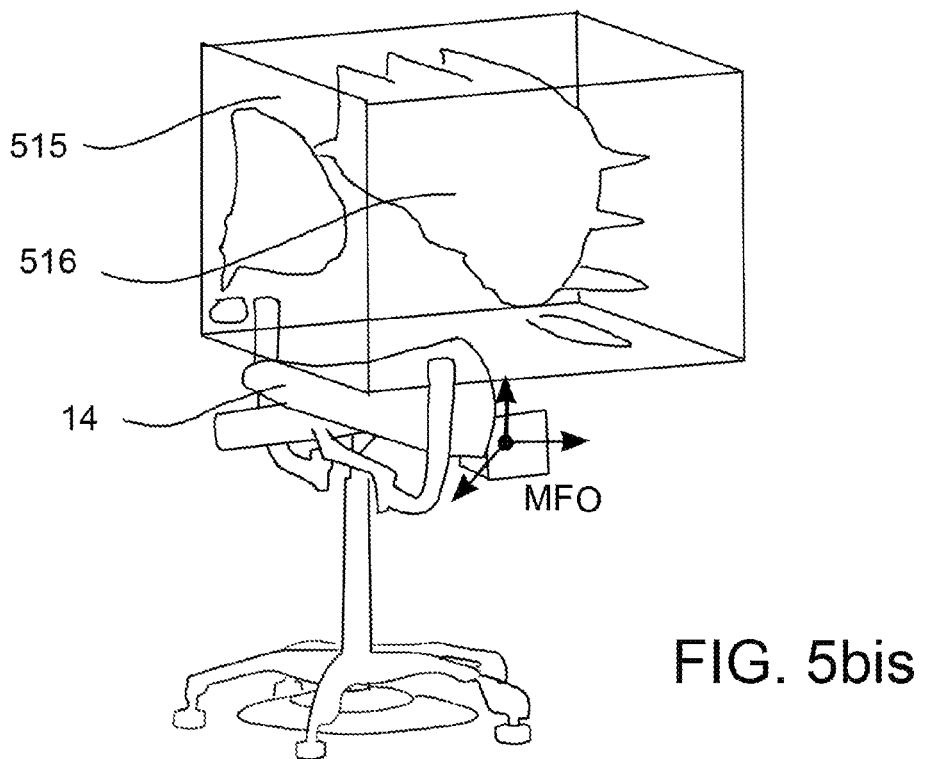
FIG. 5bis

FIG. 5ter

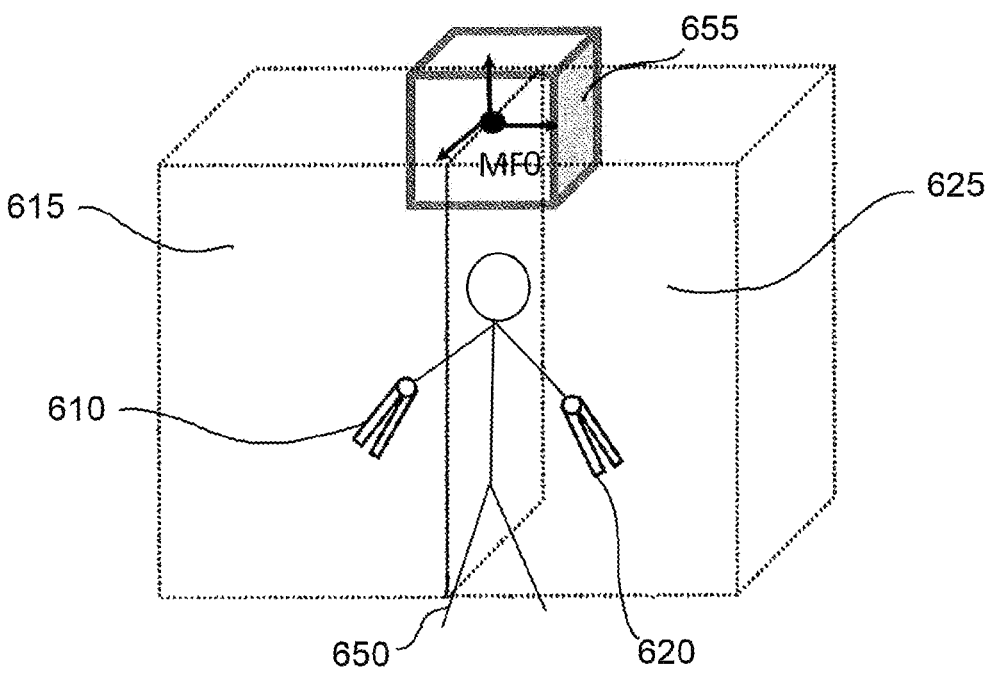
FIG. 6bis
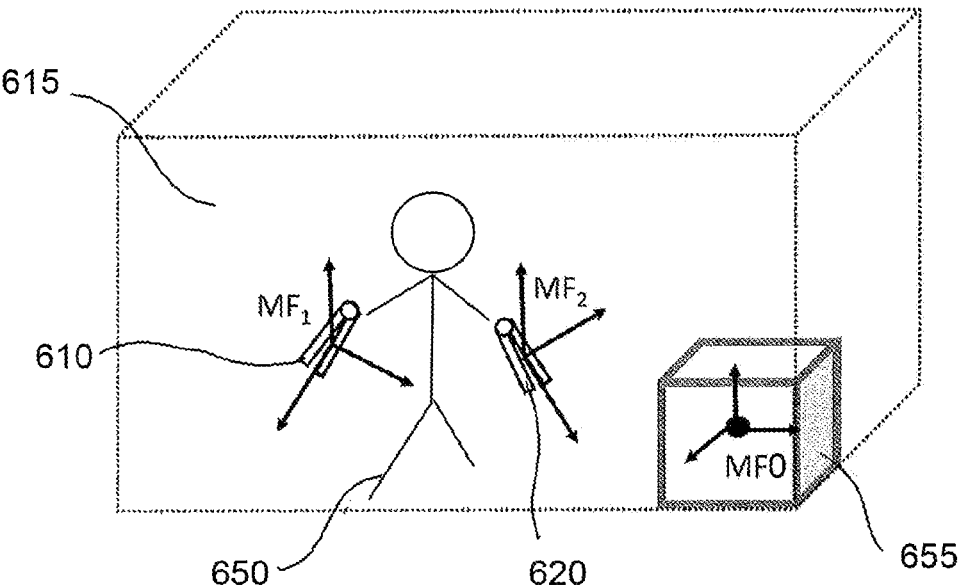
FIG. 6ter

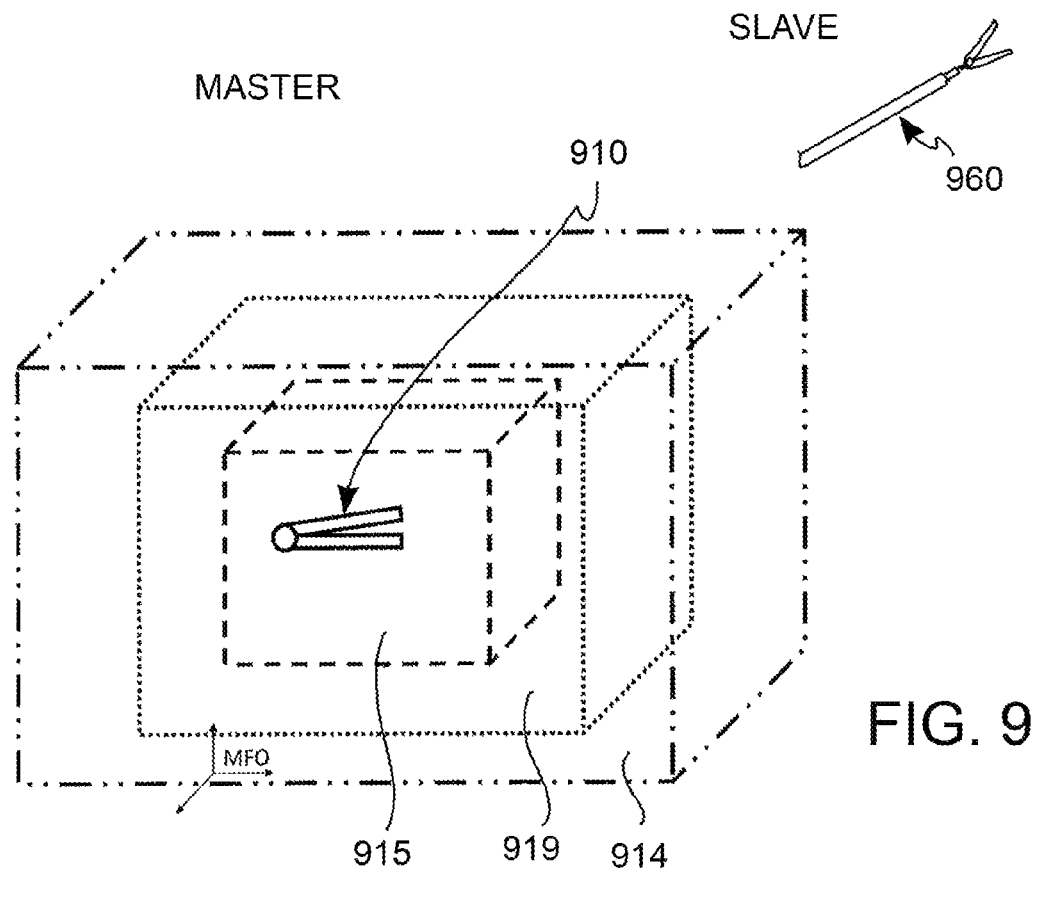
FIG. 9
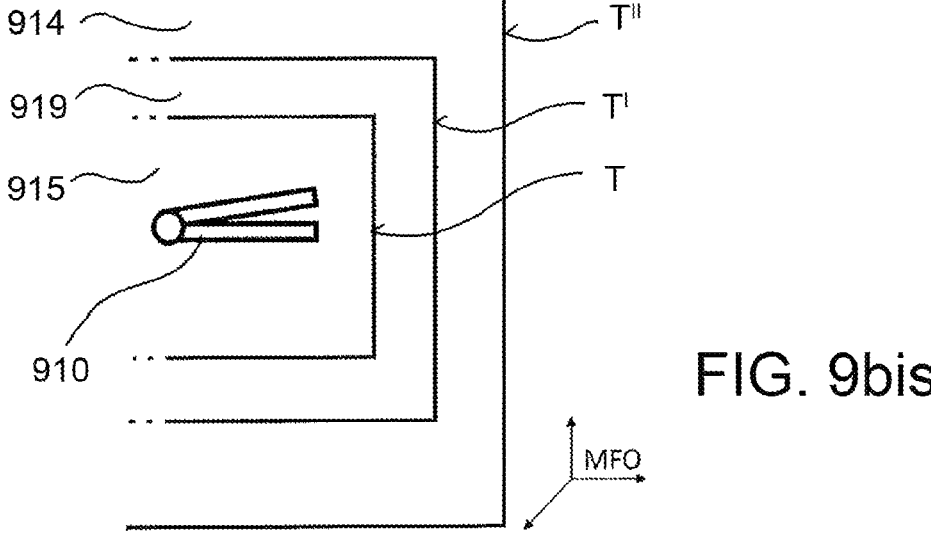
FIG. 9bis

1

METHOD FOR DETECTING OPERATING ANOMALIES OF AN UNCONSTRAINED MASTER DEVICE OF A MASTER-SLAVE ROBOTIC SYSTEM FOR MEDICAL OR SURGICAL TELEOPERATION AND RELATED ROBOTIC SYSTEM

CROSS-REFERENCE TO RELATED APPLICATIONS

The present application is a National Stage Filing of PCT International Application No. PCT/IB2022/051321 filed on Feb. 15, 2022, which claims priority to Italian Patent Application No. 102021000003422, filed on Feb. 16, 2021, which is incorporated herein by reference in its entirety.

TECHNOLOGICAL BACKGROUND OF THE INVENTION

Field of Application

The present invention relates to a method for detecting operating anomalies of an unconstrained master device of a master-slave robotic system for medical or surgical teleoperation, and a corresponding master-slave robotic system for medical or surgical teleoperation equipped so as to perform the aforesaid method.

Description of the Prior Art

In the context of robotic teleoperated surgery, with regard to master-slave robotic systems for medical or surgical teleoperation, it is very important to evaluate in real time whether the master device is functioning well and operates in the expected conditions, adapted to ensure effective action and patient safety, and it is also important to verify in real time that the master device is not operating in abnormal conditions or situations.

This need is felt both in the context of master devices with an unconstrained, magnetically or optically detected interface, and in the context of master devices with a mechanically constrained interface.

In the context of mechanically unconstrained or "ungrounded" master devices (recently emerged as an effective and advantageous solution, as for example shown in documents WO-2019-220407, WO-2019-220408 and WO-2019-220409 of the same Applicant) the aforesaid requirement poses complex technical challenges.

In particular, in a master-slave robotic system, in which the master is not mechanically constrained or motorized, the transmission of unintentional commands to the surgical (or micro-surgical) device, deriving from an uncontrolled operating situation of the master device, must be prevented to avoid risks for the patient.

The known robotic master-slave systems for medical or surgical teleoperation, with a mechanically unconstrained (or "ungrounded" or "groundless") master device, do not provide fully satisfactory solutions to the aforesaid needs, especially taking into account the very stringent safety requirements which derive from the fact that any anomaly in the operation or condition of the master device can identify consequent anomalies in the operation of the slave device and the surgical instrument associated therewith, intended to act on the patient, with possible consequences. Examples of solutions for robotic surgery having an unconstrained master are shown by documents US-2011-118748, in which the master is worn by the surgeon, and WO-2020-0092170, in which the master body has a substantially oval shape.

For example, document US-2019-380791 proposes providing an unconstrained master device with an inertial measurement unit (IMU) in addition to tracking sensors and one or more cameras, so as to compensate for the detection errors of one another, and thus estimate a quality measurement of the detection signal so that if such an estimate of the quality measurement provides a value lower than a given threshold, it enables the system to pause the teleoperation despite movements of the unconstrained master.

Therefore, in this context, the need is strongly felt to apply procedures for verifying any abnormal operating conditions of the master device in real time, conducted automatically by the robot control system for medical or surgical teleoperation, which are such as to be efficient and reliable, in order to meet the stringent safety requirements which are required by such applications.

SUMMARY OF THE INVENTION

It is the object of the present invention to provide a method for detecting operating anomalies of a master device of a robotic master-slave system for medical or surgical teleoperation, which allows at least partially overcoming the drawbacks indicated above with reference to the prior art, and responding to the needs mentioned above particularly felt in the technical field considered.

It is another object of the present invention to provide a method for managing anomalies detected in a master device comprising carrying out the method for detecting anomalies of the master device.

It is also an object of the present invention to provide a robotic system for medical or surgical teleoperation equipped to perform the anomaly detection method.

BRIEF DESCRIPTION OF THE DRAWINGS

Further features and advantages of the system and method according to the invention will become apparent from the following description of preferred embodiments, given by way of indicative, non-limiting examples, with reference to the accompanying drawings, in which:

FIGS. 1 and 2(a)-2(b) show geometric parameters and reference systems used in the method of the present invention, applied to an embodiment of the master device with a "gripper" structure;

FIG. 4bis diagrammatically shows another embodiment of a teleoperated system having a master device workspace;

FIGS. 5, 5bis, 5ter, 6, 6bis, 6ter diagrammatically show some embodiments of the aforesaid master device workspace;

FIGS. 9 and 9bis diagrammatically show some embodiments of the aforesaid master device workspace;

DETAILED DESCRIPTION

Figures 1, 2:
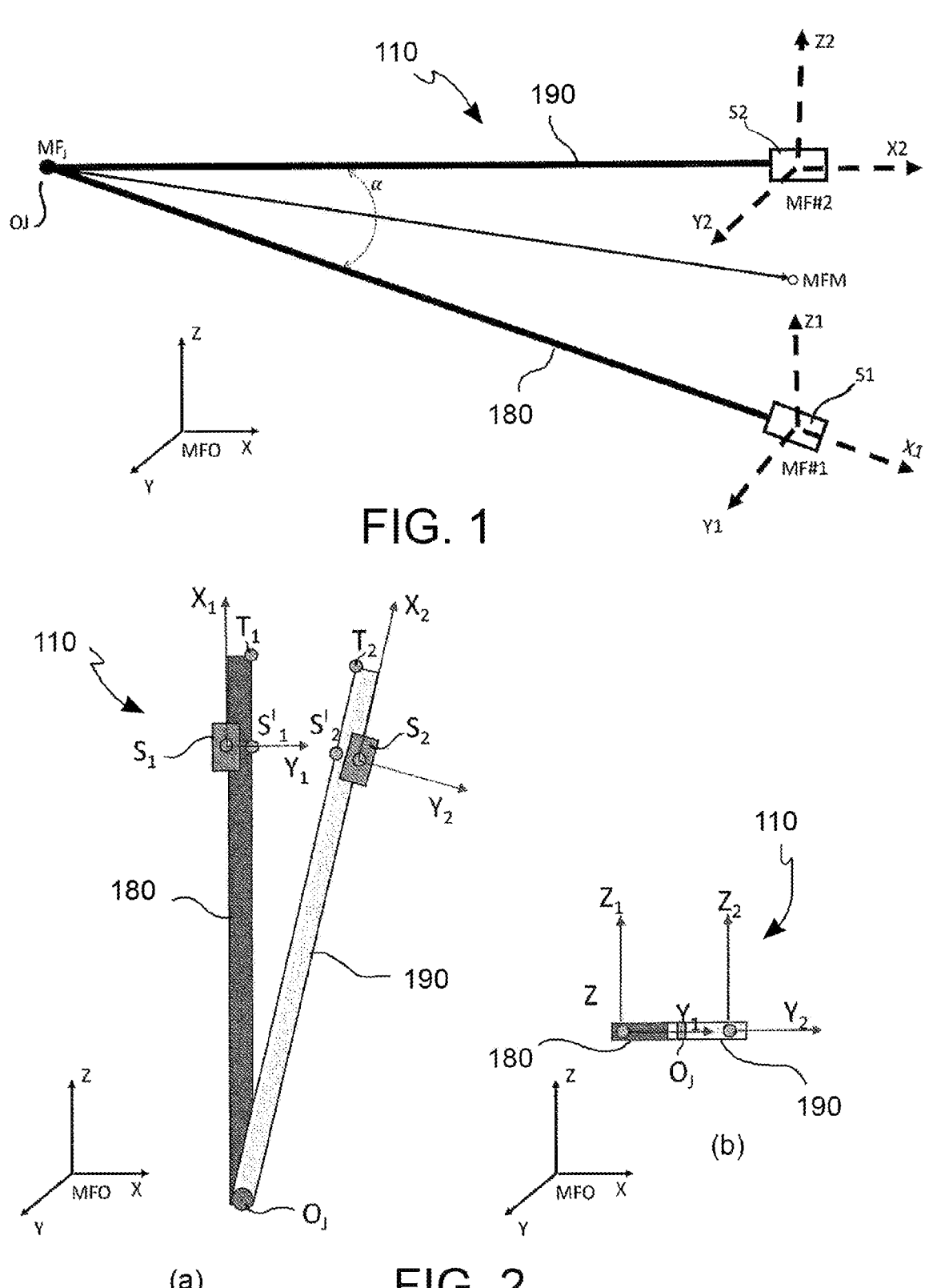

With reference to FIGS. 1-10, a method is described for identifying and recognizing and/or discriminating at least one anomaly/fault condition in the use of a hand-held master device, intended to be held (or supported) in hand by the operator, and mechanically unconstrained (i.e., mechanically ungrounded), used to control a robotic system for medical or surgical teleoperation.

Such a method comprises the steps of detecting, by one or more sensors, the position vector of at least one point belonging to or integral with the master device, or of a virtual point uniquely and rigidly associated with the master device; and then identifying and recognizing and/or discriminating at least one detectable anomaly/fault condition based on the aforesaid at least one detected position vector, or based on at least one component of the at least one detected position vector.

The aforesaid detectable anomalies/faults comprise at least an incorrect positioning of the master device with respect to a predetermined workspace of the master device.

Each of such detectable anomalies/faults is associated with at least one system state change to be performed if the anomaly/fault is detected, in which such at least one state change comprises exiting from the teleoperation state.

According to an implementation option, the identifying step comprises identifying the at least one detectable anomaly/fault condition based on at least one component of the aforesaid detected position vector.

In accordance with an embodiment, the method comprises the further step of detecting, by said one or more sensors, the evolution over time of the aforesaid position vector.

In accordance with an embodiment, the method is performed in the context of a robotic system for medical or surgical teleoperation comprising the aforesaid master device and slave device, and further comprising a control unit.

The master device is mechanically ungrounded and adapted to be held in hand by a surgeon during surgery, and is configured to detect a manual command of the surgeon and generate a respective first electrical command signal.

The at least one slave robotic assembly comprises at least one slave surgical instrument configured to operate on the anatomy of a patient, in a manner controlled by the master device, so that the movement of the master device results in a respective movement, desired and controlled, of the slave device.

The control unit provided with a computer is configured to receive the aforesaid first electrical command signal from the master device, generate a second electrical command signal, based on the first electrical command signal, and provide the second electrical command signal to the slave robotic assembly, to actuate the at least one slave surgical instrument.

Furthermore, the control unit is operatively connected to the aforesaid one or more sensors to receive at least a third electrical signal, or to receive said first electrical signal, representative of the detected position vector and/or the related evolution over time, and is configured to perform the aforesaid steps of identifying at least one detectable anomaly.

In accordance with a method embodiment, in which the detectable anomaly/fault comprises at least detecting a prohibited positioning of the master device outside predetermined spatial limits as permitted, the method comprises the following steps:

comparing the detected position of the aforesaid at least one point belonging to or integral with the master device, or virtual point uniquely and rigidly associated with the master device, with respect to a predetermined limit surface, representative of the aforesaid predetermined spatial limits;

identifying the aforesaid prohibited positioning anomaly/fault of the master device if the detected position is outside the aforesaid predetermined limit surface.

It should be noted that the aforesaid position of at least one point belonging to or integral with the master device, or virtual point uniquely and rigidly associated with the master device, and the aforesaid predetermined limit surface are defined with respect to a reference coordinate frame $(x, y, z)$ associated with the robotic system for teleoperated surgery, and having predetermined axes $(X, Y, Z)$ and origin O in a preset point. Thereby, the master device workspace is a volume having geometry defined by specific coordinates and with respect to the reference coordinate frame/system.

According to an implementation option of the aforesaid method embodiment, the aforesaid permitted spatial limits are defined as a sphere-shaped workspace or volume and the aforesaid predetermined limit surface is the spherical surface of such a sphere.

According to another implementation option of the aforesaid method embodiment, the aforesaid permitted spatial limits are defined as a workspace or volume in the form of a box or parallelepiped, or in general of a polytope (i.e., the convex intersection of half-spaces), and the aforesaid predetermined limit surface is the surface of such box or parallelepiped, or polytope.

According to a method embodiment, in which the robotic system for medical or surgical teleoperation comprises an operating console, the aforesaid reference coordinate frame is integral with the robotic system console and/or with the aforesaid at least one surgical chair.

According to an embodiment, the master device workspace is integral with and constrained to the operating console.

According to an embodiment, the master device workspace is arranged with respect to the operating console so as to contain the movements of the operator's hands and of the unconstrained hand-held master devices within a volume which ensures the operator a correct posture, mobility of the limbs and comfort.

According to an embodiment, the size and shape of the workspace are based on the posture, mobility and movements of the surgeon while operating with unconstrained master devices for safe and comfortable teleoperation.

By virtue of the provision of such a workspace with defined geometry with respect to a reference frame, for example a reference frame integral with an operating console, it is possible to optimize the posture and mobility of the surgeon while operating with an unconstrained master, to ensure a safe and comfortable teleoperation and where the master device is brought by the surgeon beyond a certain limit surface of the workspace which is integral with the console, the system limits or interrupts the teleoperation.

According to an embodiment, said operating console comprises at least one surgical chair comprising at least one seating surface for the surgeon to sit on during surgery, and the aforesaid reference coordinate system is integral with the aforesaid at least one surgical chair.

According to an embodiment, the method applies to a robotic system for surgical or medical teleoperation further comprising at least one tracking system which is suitable for detecting the input position and orientation of the master device within a predetermined tracking volume, so that the actuation of the slave surgical instrument depends on the manual command given by the surgeon by means of the master device and/or on the position and orientation of the master device.

In an implementation option of such an embodiment, the aforesaid master device workspace is contained in the aforesaid tracking volume or is a subset of the tracking volume.

By virtue of the provision of such a subset of the tracking volume, it is possible to optimize the posture, mobility and movements of the surgeon while working with unconstrained master devices for a safe and comfortable teleoperation.

In accordance with a method embodiment, said step of detecting a position is performed by one or more magnetic sensors.

Each of the magnetic sensors is arranged at a respective one of the at least one point belonging to or integral with the master device, and is configured to detect a local value of a magnetic field generated by a magnetic field generator constrained to a part of the robotic system for teleoperated surgery.

In such a case, the reference coordinate frame originates at the aforesaid magnetic emitter, and three orthogonal axes X, Y, Z.

In the case, already disclosed above, in which the robotic system comprises a tracking system, the aforesaid magnetic field generator belongs to such a tracking system.

In accordance with another method embodiment, the aforesaid step of detecting a position is performed by at least one optical sensor or camera, associated with and/or constrained to the robotic system for medical or surgical teleoperation.

In such a case, the aforesaid reference coordinate frame is an internal reference coordinate system of the optical sensor or camera.

According to different possible implementation options of the embodiment disclosed above, the aforesaid at least one optical sensor or camera is constrained to and/or integral with the surgical chair, and/or is mounted on a support which is wearable by the surgeon, so as to be integral with the surgeon.

According to a method embodiment, a teleoperation start space is predetermined, which is contained in the workspace of the master device, i.e., it is a subset of the master device workspace.

In such a case, the method includes the step of allowing the start of the teleoperation, or the start of a step of preparatory checks, only if the detected position of the master device is located within the aforesaid teleoperation start space.

According to a method embodiment, in which the master device is a hand-held, unconstrained master device, comprising two rigid parts constrained to relatively rotate or translate with respect to a common axis, the aforesaid step of detecting a position comprises detecting, by respective sensors, the position vector and/or the position vector evolution over time of at least two detectable points, a first point belonging to or integral with one of the aforesaid rigid parts of the master device and a second point belonging to or integral with the other of the aforesaid rigid parts of the device.

In fact, the method can be applied, for example, to a master device with a "gripper" structure (shown for example in FIGS. 1 and 2) having two rigid parts constrained, elastically, to rotate with respect to a common transverse axis, orthogonal to the longitudinal extension of at least one (or both) of the aforesaid rigid parts of the master device.

The method can also be applied, for example, to a master device with a "pen" structure (FIG. 10), having two rigid parts constrained, elastically, to translate along a longitudinal axis coinciding with the longitudinal extension of at least one (or both) of the aforesaid parts of the master device.

According to various possible embodiments of the method, said calculating step comprises calculating the position vector of said at least two detectable points, or calculating the position vector of one of the aforesaid at least two detected points.

According to further implementation options, the aforesaid calculating step further comprises detecting the position vector of at least one of the following further points: midpoint between said two detected points and/or center of gravity of said master device, and/or of a master device rotational joint, and/or of a master device prismatic joint.

In accordance with a method embodiment, in which the master device body comprises two tips or free ends, a first tip or free end belonging to or integral with one of the rigid parts of the master device and a second tip or free end belonging to or integral with the other of the rigid parts of the device, the aforesaid two detectable points correspond to and/or are associated with a respective one of the aforesaid two tips or free ends of the master device.

In accordance with an embodiment, when it is determined that the master device is outside the permitted spatial limits, the method comprises the further step of immediately suspending teleoperation by the robotic system. In such a case, the system state change caused by the detection of the anomaly is the immediate exit of the robotic system from the teleoperation state, or the immediate suspension of the teleoperation state.

Preferably, the permitted spatial limits define a workspace specially constructed for teleoperation, which does not correspond to the physical measuring space of the position of the master device.

According to an embodiment, when it is determined that the master device is close, within a proximity threshold E, to the aforesaid spatial limits and/or orientation limits, the method comprises the further step of communicating to the operator, by means of an acoustic and/or visual communication signal, the proximity condition of the device to the permitted spatial limits, so as to allow the operator to act so as to avoid exiting the spatial limits and thus exiting the teleoperation.

According to an implementation option, the aforesaid communication signal is an acoustic signal, which increases the frequency thereof as the distance of the master device or the slave device from the spatial limit decreases, in the interval between the proximity threshold s and the surface corresponding to the spatial limit.

According to an implementation option, the aforesaid communication signal is a visual signal; the frequency of the communication of the visual signal increases as the distance of the master device or of the slave device from the spatial limit decreases, in the interval between the proximity threshold s and the surface corresponding to the spatial limit.

According to various possible implementation options of such an embodiment, the method further includes allowing the restart of the teleoperation of the robotic system when it is detected, in real time, that the master device has returned to the permitted spatial limits; or, alternatively, to inhibit the restart of the teleoperation of the robotic system even if it is detected, in real time, that the master device has returned to the permitted spatial limits, and to restart procedures for preparing and starting teleoperation and/or preliminary realignment operations. The aforesaid permitted spatial limits are defined by the master device workspace or by the teleoperation start space.

According to an embodiment, the master device workspace is defined as a teleoperation volume in which it is possible to move the slave device in teleoperation.

According to an embodiment, around the aforesaid teleoperation volume, a suspended teleoperation volume, in which the machine provides for a limited teleoperation, is defined.

More in detail, the suspended teleoperation volume extends around the master device workspace and is larger than the master device workspace; such suspended teleoperation volume is a volume in which the robotic system provides for a suspended teleoperation, which corresponds to a limited teleoperation.

Preferably, such a limited teleoperation prevents the translation movements of the control point. According to another implementation option, the limited teleoperation prevents any movement of the slave device.

In the aforesaid embodiment which provides a suspended teleoperation, the method includes the further step of switching from the teleoperation state to the suspended teleoperation state when the master device exits the workspace limits and enters the suspended teleoperation volume.

In an implementation option, the entry or exit from the suspended teleoperation volume is indicated to the user with an acoustic and/or visual and/or tactile signal.

According to an embodiment, upon exceeding the thresholds of the teleoperation volume and/or upon exceeding the external thresholds of the suspended teleoperation volume, the teleoperation is terminated.

In an embodiment, the method comprises the step of permitting the robotic system to return to the teleoperation state, with the restart of teleoperation, when it is detected that the master device has returned from the suspended teleoperation volume within the workspace limits.

In an embodiment, upon switching the master from the suspended teleoperation volume to the teleoperation volume, the system enters a step of alignment with motion, in which the slave device is enabled to move to reach the new pose (position, orientation) of the master device.

In an implementation option, the step of alignment with motion enables only the orientation of the control point of the surgical instrument of the slave device to move.

According to an implementation option, it is possible to move the orientation and degree of freedom of opening/closing freedom ("grip") of the surgical instrument of the slave device.

In an embodiment, the entry into the step of alignment with motion is permitted only if some verification checks are passed, said verification checks comprising at least the following checks: misalignment in master-slave orientation below a certain threshold, and/or orientation pose of the master being reachable within the slave workspace.

According to a method embodiment, in which the movements of the master device and the slave device are scaled by a scale factor, the aforesaid workspace of the slave device and/or teleoperation start space and/or suspended teleoperation volume grow with the scale factor.

According to a method embodiment, in which the robotic system comprises two master devices, and in which the method includes exiting the teleoperation and/or suspending the teleoperation of both master devices if even only one of the master devices exits the permitted spatial limits.

In accordance with another embodiment, the method comprises the further step of verifying that the slave device is within a permitted slave device workspace.

In such a case, if the slave device is verified to be outside the permitted slave device workspace, the method comprise notifying the user that a slave device positioning anomaly has emerged, and immediately stopping the teleoperation by the robotic system.

According to various possible implementation options of such an embodiment, the method further includes allowing the restart of the teleoperation of the robotic system when it is detected, in real time, that, following a further movement of the master device, the slave device has returned to the permitted spatial limits of the slave device; or, alternatively, the method includes inhibiting the restart of the teleoperation of the robotic system even if it is detected, in real time, that the slave device has returned to the permitted spatial limits of the slave device, and restarting procedures for preparing and starting teleoperation and/or preliminary realignment operations.

According to an implementation option of the method, the slave device workspace comprises the spatial set of all the positions which are reachable by a control point of the slave device as a consequence of the possible poses and/or orientations of the articulated surgical instrument (or "end effector") of the slave device.

In accordance with an embodiment, the method comprises the further step of calculating linear velocity and/or angular velocity and/or linear acceleration and/or angular acceleration of said at least one point belonging to or integral with the master device, or virtual point associated uniquely and rigidly with the master device, based on the evolution over time of the respective position vector detected.

In accordance with another embodiment, the method comprises the further step of calculating the linear or angular velocity of the aforesaid at least one point belonging to or integral with the master device, or a virtual point uniquely and rigidly associated with the master device, based on the temporal evolution of the respective position vector detected.

A further aspect of the invention is now described, again with reference to FIGS. 1-10, again related to a method for identifying and recognizing and/or discriminating at least one anomaly/fault condition in the use of a hand-held master device, suitable to be held (or supported) by the operator, and mechanically unconstrained (i.e., ungrounded), used to control a robotic system for medical or surgical teleoperation.

Such a method comprises the steps of detecting or calculating the velocity vector of at least one point belonging to or integral with the master device, or of a virtual point uniquely and rigidly associated with the master device; and identifying and recognizing and/or discriminating at least one detectable anomaly/fault condition based on the aforesaid at least one detected velocity vector, or based on at least one component of the at least one detected position vector.

The aforesaid detectable anomalies/faults comprise at least one of the following anomalies/fault: excessive linear velocity of the master device, excessive angular velocity of the master device, inability to follow by the slave device, excessive vibrations of the master device, involuntary or abnormal opening of the master device.

Each of the aforesaid detectable anomalies/faults is associated with at least one system state change to be performed if the anomaly/fault is detected. Such a state change comprises exiting from the teleoperation state or suspending the teleoperation state.

According to a method embodiment, the step of detecting or calculating a velocity vector comprises:

detecting the position vector, and the evolution over time of the position vector, of the aforesaid at least one point belonging to or integral with the master device, or of the aforesaid at least one virtual point uniquely and rigidly associated with the master device;

calculating the velocity vector of the aforesaid at least one point belonging to or integral with the master device, or of the aforesaid at least one virtual point uniquely and rigidly associated with the master device, based on the aforesaid position vector and respective evolution over time detected.

According to another method embodiment, the step of detecting or calculating a velocity vector comprises: detecting the velocity vector by one or more velocity sensors.

In accordance with a method embodiment, a linear velocity of the at least one point belonging to or integral with the master device, or of the at least one virtual point uniquely and rigidly associated with the master device, is detected or calculated.

In accordance with another method embodiment, an angular velocity of the at least one point belonging to or integral with the master device, or of the at least one virtual point uniquely and rigidly associated with the master device, is detected or calculated.

According to an embodiment, the method is applied to a robotic system for medical or surgical teleoperation comprising:

the aforesaid master device, mechanically ungrounded and adapted to be held in hand by a surgeon during surgery, and configured to detect a manual command of the surgeon and generate a respective first electrical command signal;

at least one slave robotic assembly, comprising at least one slave surgical instrument configured to operate on the anatomy of a patient, in a manner controlled by the master device, so that the movement of the master device results in a respective movement, desired and controlled, of the slave device;

a control unit provided with a computer, configured to receive the aforesaid first electrical command signal from the master device, generate a second electrical command signal, based on the first electrical command signal, and provide the second electrical command signal to the slave robotic assembly, to actuate the at least one slave surgical instrument.

The control unit is operatively connected to said one or more sensors to receive at least a third electrical signal representative of said detected or calculated velocity vector.

The aforesaid step of identifying and recognizing and/or discriminating at least one detectable anomaly/fault is performed by such a control unit.

In accordance with an embodiment, the velocity vector is referred to a reference coordinate frame.

According to an implementation option, the robotic system for medical or surgical teleoperation comprises an operating console, and the aforesaid reference coordinate frame is integral with the aforesaid robotic system console.

According to an implementation option, the method applies to a robotic system for surgical or medical teleoperation further comprising at least one tracking system which is suitable for detecting the input position and orientation and/or velocity of the master device within a predetermined tracking volume, so that the actuation of the slave surgical instrument depends on the manual command given by the surgeon by means of the master device and/or on the position and orientation of the master device.

In such a case, the aforesaid reference coordinate frame is defined by said tracking system.

According to an implementation option of the method, in which the master device is an unconstrained, hand-held master device, comprising two rigid parts constrained to relatively rotate or translate with respect to a common axis, the aforesaid step of detecting and/or calculating a velocity comprises detecting and/or calculating the linear or angular velocity of at least two detectable points, a first point belonging to or integral with one of the rigid parts of the master device and a second point belonging to or integral with the other one of the rigid parts of the device;

According to another implementation option of the method, but still referring to the same configuration of the master device, the aforesaid step of detecting and/or calculating a velocity comprises detecting and/or calculating the linear or angular velocity of the at least two detectable points, and/or the linear or angular velocity of at least one of the following further points: midpoint between the two detected points and/or center of gravity of the master device, and/or of a rotational joint of the master device, and/or of a prismatic joint of the master device.

According to an implementation option, the master device body comprises two free ends or tips, a first free end or tip belonging to or integral with one of the rigid parts of the master device and a second free end or tip belonging to or integral with the other of the rigid parts of the device. In such a case, the aforesaid two detectable points correspond and/or are respectively associated with the aforesaid two free ends or tips of the master device.

According to a method embodiment, when even only one of the aforesaid anomalies/faults is determined, the change of state imposed on the system is the immediate exit of the robotic system from the teleoperation state, or the immediate suspension of the teleoperation state.

According to an implementation option of the aforesaid embodiment, the method further comprises allowing the restart of the teleoperation of the robotic system when the termination of the previously detected anomaly/fault is detected, in real time.

According to an implementation option of the aforesaid embodiment, the method provides instead the step of inhibiting the restart of the teleoperation of the robotic system even if the cessation of the previously detected anomaly is detected in real time, and restarting procedures for the preparation and start of teleoperation and/or preliminary realignment operations.

In accordance with an embodiment, in which the detectable anomaly/fault is an anomaly/fault associated with an excessive linear or angular velocity of the master device, the method comprises the following steps: comparing the detected linear or angular velocity of the master device with a linear or angular velocity threshold value; and identifying the aforesaid anomaly associated with an excessive velocity of the master device if the detected linear or angular velocity of the master device exceeds said linear or angular velocity threshold value.

According to an implementation option of such an embodiment, when said anomaly associated with an excessive linear or angular velocity of the master device is detected, the robotic system exits the teleoperation.

According to an implementation option of such an embodiment, when the aforesaid anomaly/fault associated with an excessive linear or angular velocity of the master device is detected, the robotic system enters a different machine state.

According to an implementation option, such a different machine state is a suspended teleoperation state, i.e., a limited teleoperation which prevents at least the translation movements of a control point of the slave device, or which limits the rotational movements of the control point of the slave device, or which prevents all movements of the control point of the slave device.

According to another implementation option, in the aforesaid limited teleoperation step, the method comprises carrying out a step of alignment with motion in which the slave device moves in orientation, aligning itself with the orientation of the master device while the translation of the slave device is inhibited.

In accordance with an embodiment, in which the detectable anomaly/fault is an anomaly/fault associated with an inability to follow by the slave device, the method comprises the steps of: comparing the detected linear or angular velocity of the master device with a velocity threshold value associated with a maximum linear or angular velocity, tolerable by the slave device to remain in a condition of correctly following the master device; and identifying the aforesaid anomaly/fault associated with an inability to follow by the slave device if the detected linear or angular velocity of the master device exceeds the aforesaid velocity threshold value associated with a maximum tolerable linear or angular velocity.

In accordance with an embodiment, in which the detectable anomaly/fault is an anomaly/fault associated with excessive vibrations of the master device, the method comprises the steps of: detecting or counting the number or frequency of direction changes of the detected or calculated velocity vector of the master device; then, comparing said number or frequency of direction changes with a respective threshold value; and finally, identifying the aforesaid anomaly/fault associated with excessive vibrations of the master device if the number or frequency of direction changes, counted or detected, exceeds the aforesaid respective threshold value.

According to an embodiment, in which, again, the detectable anomaly/fault is an anomaly/fault associated with excessive vibrations of the master device, the method comprises the steps of: detecting movements and/or variations of the velocity vector modulus; then, detecting the aforesaid anomaly/fault associated with excessive vibrations of the master device if the movements and/or variations of the velocity vector modulus exceed a respective threshold.

In accordance with an embodiment, in which the master device body comprises two rigid parts constrained in a joint, preferably an elastic joint, to at least rotate about a common axis defining a degree of freedom of opening/closing for the master device body, the detectable anomaly/fault is an involuntary or abnormal opening of the master device.

According to an implementation option of such an embodiment, the method comprises the following steps:

calculating the opening linear velocity of the two rigid parts of the master device body, based on the detected and/or calculated velocity vectors;

comparing the calculated opening linear velocity with a threshold linear velocity $v\_thr$, which can depend on the elastic rigidity of the elastic joint;

identifying the anomaly/fault condition associated with an involuntary opening of the master device if the aforesaid calculated opening velocity is greater than the aforesaid threshold linear velocity $v\_thr$.

According to another implementation option of such an embodiment, the method comprising the following steps:

calculating the opening angular velocity of the two rigid parts of the master device body, based on the detected and/or calculated velocity vectors;

comparing the calculated opening angular velocity with a threshold angular velocity $\omega\_thr$, which can depend on the elastic rigidity of the elastic joint;

identifying the anomaly/fault condition associated with an involuntary opening of the master device if the aforesaid calculated opening angular velocity is greater than the aforesaid threshold angular velocity $\omega\_thr$.

In accordance with an embodiment, in which the detectable anomaly/fault is an anomaly/fault associated with a displacement of the origin of the tracking reference system, the method comprises the following steps:

calculating the linear velocity of each real or virtual sensor used for the position measurements of the master device;

calculating if within a given time window each velocity vector can be expressed with a primary constant component;

calculating if all the resulting velocity vectors are mutually parallel and coherent, or if they belong to an adequate velocity vector region;

identifying the anomaly/fault associated with a displacement of the origin of the reference tracking system if the aforesaid condition of mutually parallel and coherent velocity vectors, or belonging to an adequate velocity vector region, does not occur.

According to an embodiment, the method includes detecting all the detectable anomalies/faults mentioned hereafter: excessive linear velocity of the master device, excessive angular velocity of the master device, inability to follow by the slave device, excessive vibrations of the master device, involuntary or abnormal opening of the master device.

According to an embodiment, in which the robotic system comprises two master devices, the method includes exiting the teleoperation and/or suspending the teleoperation of both master devices if even only one of the master devices is affected by any one of the aforesaid detectable anomalies/faults.

A method for managing anomalies/faults identified in a master device of a master-slave robotic system for surgical or medical teleoperation is now described.

Such a method comprises the steps of performing a method for identifying at least one anomaly/fault condition according to any of the embodiments described above; if at least any of the anomalies/faults is determined, the method includes immediately stopping or suspending the teleoperation and movements of the surgical instrument of the slave device.

In accordance with an embodiment, the method comprises the further step of detecting, by acceleration sensors, the linear or angular acceleration of at least one point belonging to or integral with the master device, or of a virtual point uniquely and rigidly associated with the master device.

According to another embodiment, already mentioned above and further detailed here, the method includes calculating, based on the aforesaid detected position vector or the aforesaid detected or calculated velocity vector, or the respective evolutions over time, the linear or angular acceleration of at least one point belonging to or integral with the master device, or of a virtual point uniquely and rigidly associated with the master device.

According to an implementation option of such an embodiment, the aforesaid step of detecting and calculating the acceleration vector comprises calculating the acceleration vector by floating windows of N samples of the vector representing the position vector evolution over time, and by interpolation with second order polynomials, for the degree of freedom related to the grip, and with third order polynomials, for the degrees of freedom related to the master device translation and orientation.

In accordance with an implementation option, the acceleration is calculated based on the detection of the velocity vector and the temporal evolution thereof.

According to an implementation option, the acceleration is directly detected by one or more sensors, in which such one or more sensors are accelerometers.

According to various possible embodiments of the method, as a basis for detecting anomalies/faults, for each of the aforesaid at least one points belonging to or integral with the master device, or virtual point uniquely and rigidly associated with the master device, the linear acceleration and/or the angular acceleration and/or the linear velocity and/or the angular velocity and/or the position in Cartesian coordinates and/or the position in polar or angular coordinates are calculated or detected.

In accordance with a method embodiment, the aforesaid step of detecting and/or calculating the acceleration vector comprises detecting and/or calculating by at least two sensors the acceleration vector of each of at least two points belonging to or integral with the master device; and then calculating the acceleration vector of a virtual point uniquely and rigidly associated with the master device, corresponding to the midpoint between the points where the sensors are located.

For example, in a "gripper" master device, such a midpoint can be located on the opening circumference arc described by the one or more sensors of the "gripper" master device.

If there is only one control point, 6 degrees of freedom, i.e., 3 degrees of position and 3 degrees of orientation, can be detected.

If two control points are provided, it is also possible to detect a seventh degree of freedom, associated with the grip, representative of the opening/closing angle of the master device body.

In accordance with an embodiment, the method comprises the further step of detecting, based on the aforesaid acceleration vector, one or more further anomalies/faults among the ones mentioned hereafter: involuntary drop of the master device and/or excessive acceleration of the master device and/or sudden and involuntary opening of the master device.

In accordance with a method embodiment, in which the detectable anomaly/fault is an involuntary drop of the master device, the method comprises the following steps:

detecting and/or calculating the vertical acceleration component ay, parallel to the gravity axis, of at least one of the two detected points;

comparing the detected or calculated vertical acceleration component ay with a vertical acceleration threshold ay_thr;

identifying the anomaly/fault associated with the involuntary drop of the master device if the aforesaid vertical acceleration component ay is greater than the aforesaid vertical acceleration threshold (ay_thr), according to the relation: ay>ay_thr.

According to an implementation option the vertical acceleration threshold value ay_thr is equal to the gravity acceleration g, or is a value around g.

According to an implementation option, the acceleration vector of each of the aforesaid at least two detection points of the master device is calculated to provide redundancy and/or a further verification.

In fact, the consistency of the calculated acceleration measurement of the aforesaid at least two points makes it possible to improve the estimation of the anomaly determination, further reducing the time window necessary for the estimation process.

An inconsistency of the calculated measurement of acceleration of the two points can be associated with a drop with rotation of the master device, or the breakage of the rigid constraints between the two sensors.

In the specific case of mounting two sensors in the same mechanical part of the master device, the behavior of the measurements is pure redundancy.

In accordance with a method embodiment, in which the detectable anomaly/fault is an excessive acceleration of the master device (e.g., imparted in the handling by the user), the method comprises the following steps:

detecting and/or calculating the acceleration vector modulus atot of at least one of the aforesaid at least two detected points;

comparing the detected and/or calculated acceleration vector modulus atot with a total acceleration threshold atot_thr;

detecting the anomaly associated with an excessive acceleration of the master device if the aforesaid acceleration vector modulus atot is greater than the aforesaid total acceleration threshold atot_thr, according to the relation: atot>atot_thr.

According to an implementation option, said vertical acceleration threshold ay_thr is lower than said total acceleration threshold atot_thr.

For example, the relation can be used: atot=3·ay.

In accordance with an implementation option, the total acceleration threshold value atot_thr (in modulus) belongs to the range between 2 g and 4 g.

According to an embodiment, the accelerations of both detection points of the master device are calculated.

According to different possible implementation options of such an embodiment, the alarm trigger condition is raised if at least one of the aforesaid detected points exceeds the threshold acceleration, or if the virtual midpoint exceeds the threshold acceleration, or if the relative acceleration between the aforesaid two points is above threshold.

According to an implementation option, the aforesaid total acceleration threshold atot_thr is defined so as to increase with the decrease of the scaling factor of the motion between the master device and the slave device, and/or with the decrease of a scaling factor selected by the user and applied to the teleoperated Master-Slave movement.

According to an application example, in the field of robotic micro-surgery, the scaling factor can be defined in a range between 7× and 20×. Obviously, the greater such a scaling factor (for example, the slave movement is scaled 20×), the greater the trigger threshold.

It should be noted that, in a typical implementation option, the scaling factor can be set by the user depending on the specific circumstances.

In accordance with a method embodiment, in which the master device consists of two rigid parts mutually connected in an elastic joint which tends to open such parts at least angularly when not pressed or held firmly in the user's hand, the detectable anomaly/fault is an involuntary opening of the master device. Such a situation can occur, in particular, if the surgeon loses control, for example because the master device has escaped his hands, and the master device, dropping, opens by snapping due to the spring of the joint.

In such a case, the method comprises the following steps:

detecting and/or calculating the acceleration vector (as previously disclosed) and/or the respective evolution over time of each of said two detectable points;

calculating the opening angular velocity $\omega$ of the two rigid parts of the master device, based on the aforesaid detected and/or calculated acceleration vectors;

comparing the calculated opening angular velocity $\omega$ with a threshold angular velocity $\omega\_thr$ which depends on the elastic rigidity of the elastic joint;

identifying the anomaly/fault condition associated with an involuntary opening of the master device if the aforesaid calculated opening angular velocity $\omega$ is greater than the aforesaid threshold angular velocity ($\omega\_thr$).

According to similar implementation options, the aforesaid steps of calculating, comparing and identifying are performed not on the angular velocity, but on the angular acceleration, or on the linear acceleration.

According to another implementation option, again referring to the case in which the master device consists of two rigid parts mutually connected in an elastic joint which tends to open such parts at least angularly when not pressed or held firmly in the user's hand, and the detectable anomaly/fault is an involuntary opening of the master device, the method comprises the following steps:

detecting the position vector and the respective evolution over time of each of the two detectable points;

calculating the evolution over time of the distance between the aforesaid two detectable points, based on the evolution over time of the position vectors detected;

calculating the opening linear velocity v of the master device, based on the evolution over time of the aforesaid distance;

comparing the calculated opening linear velocity v with a threshold linear velocity $v\_thr$;

identifying the aforesaid anomaly condition if $v > v\_thr$.

In accordance with a method embodiment, the aforesaid anomalies/faults of detecting a prohibited positioning of the master device outside predetermined spatial limits, detecting a prohibited positioning of the slave device outside predetermined spatial limits, excessive velocity of the master device, inability to follow by the slave device, excessive vibrations of the master device, and further involuntary drop of the master device, excessive acceleration of the master device and sudden and involuntary opening of the master device are all detected, and at the same time.

Advantageously, such an embodiment allows a wide spectrum of controls to be obtained, aiming at the maximum possible safety.

A method for managing anomalies found in a master device of a master-slave robotic system for surgical or medical teleoperation is further comprised in the present invention.

Such a method includes performing a method for identifying at least one anomaly condition according to any one of the embodiments described above.

Such a method further comprises, if at least any one of the aforesaid anomalies/fault are determined, the step of immediately interrupting or suspending the teleoperation and the movements of the surgical instrument (or "end-effector") of the slave device, to safeguard the patient's safety.

Making reference again to FIGS. 1-10, a robotic system for medical or surgical teleoperation comprised in the present invention is described herein.

Such a robotic system comprises at least one master device, at least one slave device, and a control unit.

The at least one master device is mechanically ungrounded and adapted to be held in hand by a surgeon during surgery, and is configured to detect a manual command of the surgeon and generate a respective first electrical command signal.

The at least one slave device, or slave robotic assembly, comprises at least one slave surgical instrument configured to operate on the anatomy of a patient, in a controlled manner by the respective at least one master device.

The control unit provided with a computer is configured to receive the aforesaid first electrical command signal from the master device, generate a second electrical command signal, based on the first electrical command signal, and provide the second electrical command signal to the slave robotic assembly, to actuate the at least one slave surgical instrument.

The control unit of the robotic system is configured to carry out the following actions:

detecting, by means of one or more sensors (S1, S2; 585, 595; 785, 795; 885, 895) with which the control unit is operatively connected, the position vector of at least one point belonging to or integral with the master device, or of a virtual point uniquely and rigidly associated with the master device;

identifying and recognizing and/or discriminating at least one detectable anomaly/fault condition based on the aforesaid at least one detected position vector, or based on at least one component of the at least one detected position vector.

The aforesaid detectable anomalies/faults comprise at least an incorrect positioning of the master device with respect to a predetermined workspace (315; 415; 415, 425; 515; 615; 615, 625; 715; 815; 915) of the master device.

Each of the aforesaid detectable anomalies/faults is associated with at least one system state change to be performed if the anomaly/fault is detected, in which such at least one state change comprises exiting from the teleoperation state.

According to different embodiments of the robotic system, the control unit of the robotic system is further configured to perform a method for identifying at least one anomaly/fault condition according to any one of the embodiments shown in the present description.

According to an embodiment of the robotic system, the control unit of the robotic system is further configured to perform a method for managing anomalies/faults identified in a master device of a master-slave robotic system according to any one of the embodiments shown in the present description.

In accordance with an embodiment of the robotic system, a suspended teleoperation volume 919 is defined, which extends around the master device workspace and is larger than the master device workspace. Such a suspended teleoperation volume is a volume in which the robotic system provides for a suspended teleoperation, i.e., a limited teleoperation which prevents at least the translation movements of a control point of the slave device, or which limits the rotational movements of the control point of the slave device, or which prevents all movements of the control point of the slave device.

In such a case, the control unit of the robotic system is further configured to cause the switching from the teleoperation state to the suspended teleoperation state when the master device exits the workspace limits and enters the suspended teleoperation volume.

In an implementation option of the system, the master device body comprises seats for receiving the one or more sensors in respective predeterminable positions.

According to a system embodiment, the master device body is disposable and thus typically made of plastic.

According to another embodiment of the system, the master device body is made of metal (e.g., titanium) and is sterilizable.

With reference to FIGS. 1-10, some embodiments of the method, previously defined in more general terms, will be further detailed below, by way of non-limiting example.

The anomaly checks of the master device are introduced into the robotic system for teleoperation in order to intervene with the minimum latency with respect to the actual movement.

In an embodiment, the sequence of operating actions carried out includes an acquisition of information on all the degrees of freedom of movement of the master device, for example in terms of acceleration; then, filtering the signals obtained; evaluating one or more anomaly/fault checks on the master; detecting any faults or anomalies of the master device, based on the controls carried out; communicating with the control unit of the machine state of the robotic system, with the user interface UI and with the end points of the slave device.

Further details on the anomaly/fault checks carried out in some embodiments of the method (already mentioned) will be provided below, by way of non-limiting example.

Drop of the master device ("master drop").

The objective of this check is to identify an involuntary drop of the master device from the surgeon's hands. Such a check is based on the detection of acceleration (or position) of the master device (without the need for further sensors for detecting other quantities, such as pressure-sensitive surfaces).

The principle consists in detecting the acceleration, or in deriving the acceleration from position information (even affected by noise) and calculating the instantaneous value of the acceleration along the (downwards) direction of the gravity vector.

When such an acceleration reaches a threshold which is comparable to the acceleration of gravity, the anomaly warning is issued with respect to this check.

It is assumed below that, in the Global Reference System, the gravitational field is oriented along the −Y axis.

For example, the acceleration estimation is based on the use of a polynomial fitting of the Y axis, and then the double derivation of the polynomial by manipulating the coefficients thereof.

Among the different usable fitting techniques, for example, the solution based on the Solezky-Golay filter can be mentioned. This solution is characterized in that it expresses the polynomial derived as in the FIR (Finite Impulse Response) filter, which operatively consists of taking a window of 2W+1 samples and multiplying it by a matrix. Such a matrix depends on two parameters: the size of the window (with half-width W) and the order of the polynomial.

The size of the window depends on the sampling time, the desired latency in computation, and the signal noise.

The order of the polynomial depends on the nature of the positional signal.

The filter is a low-pass filter, with cutoff frequency which can be expressed according to relations known in the literature, for example:

$$\text{Cutoff (Hz)} = Dt^* (\text{Order}+1)/(3.2^*\text{Window}-4.6)$$

According to an implementation option, the master device has two detection positions (i.e., two sensors). In such a case, when any one thereof exceeds the threshold, an anomaly warning is issued.

It should be noted that the wider the window used for the estimate, the better the estimate itself, with the aforesaid algorithm. On the other hand, the narrower the window, the faster the reaction time.

A criterion for choosing an appropriate compromise between the aforesaid needs is the amount of space traveled by the controlled slave device during the unintuitive and undesired movement of the master device (for example, the dropping movement of the master). The maximum distance allowed to the path by the controlled slave device during the non-intuitive movement defined as D, and the maximum velocity of the master in this situation defined as M, then the maximum window width W is expressed by the relation:

$$W=2D/M/T+1,$$

where T is the sampling time.

Exceeding a Maximum Acceleration

Another type of anomaly check is related to an unintuitive movement is an excess acceleration of the master device along any direction. This event can be identified based on a detection or estimation of acceleration component by component, using the same techniques described above for the "Master Drop" case.

In this case, the vector modulus of the three components is compared with a threshold to issue any anomaly warning.

Sudden Opening of the Master Device.

In the case of a master device having a degree of freedom related to the grip, a further check can be performed on a possible excessively fast opening of the grip of the master device, which is considered indicative, for example, of the anomaly situation in which the operator loses control of the master device, or of the grip on the master device.

The estimation of the opening velocity is performed, for example, using the same polynomial fitting described above for the "Master Drop" case, but with different parameters, associated with this particular condition.

The estimated velocity of the opening angle (or "grip angle") obtained from the fitting is used for the evaluation of this anomaly.

Master Device Outside Spatial Limits.

Another anomaly check is related to the spatial limits prescribed for operator movement. These limits are defined based on usability considerations of the specific surgical target and limitations of the sensor system used to calculate the position of the master device.

Two main scenarios can be identified in relation to such limits: a sphere centered in the center of the workspace; or a parallelepiped or box-shaped surface.

When the limits of such volumes are reached by the master device, an anomaly notification is provided to the user.

In the context of a master device with constrained mechanical interface, these limits depend on the limits of the mechanical interface.

In the context of a master device with an unconstrained mechanical interface, if an optical detection is considered, the workspace is the intersection of the cone trunks of each camera, built taking into account the minimum resolution necessary to identify the features being tracked. When considering magnetic tracking systems, the workspace has limits which depend on the attenuation of the magnetic field.

Preferably, the "workspace" is a workspace specially constructed for teleoperation. Therefore, "workspace" is not intended to indicate the physical space beyond which it is not possible to detect measurement information, but a narrower space defined and acceptable specifically for the activity of surgical teleoperation. For example, the "workspace" is the region of space within which the posture, mobility and movements of the surgeon while operating with unconstrained master devices is optimized for safe and comfortable teleoperation. The definition, evaluation, and management of the workspace volume of an unconstrained master are beneficial for the usability of the surgeon because they allow warning the operator of having reached a work region in which his posture leads to a reduction of his comfort and a reduction of the mobility of the arm-hand structure, such as a very forward posture with respect to the seat or conversely with the hand and arm too close to the torso; moreover, the exit from the defined workspace can signal an incorrect action by the surgeon.

For example, the "workspace" is the region of space in which the signal quality criterion (noise) is within acceptable thresholds, and/or the "workspace" is a selected work region with respect to usability, such as the surrounding position with respect to the occupied position of the operator.

According to an embodiment, three workspaces related to the master device are defined, in which the aforesaid three workspaces are preferably at least partially interpenetrated:
1. "Master Measurable Workspace": this is the work volume within which valid position or rotation information of the master device can be obtained, even if affected by error values which are unacceptable for teleoperation. Such a work volume has an arbitrary geometric shape, referring to the origin of the measurement system. The shape can depend on the type of measurement, for example: cone in the case of an optical measurement system, cut half-spheres in the case of a magnetic measurement system.
2. "Operator Usable Workspace": this is the work volume within the "Master Measurable Workspace" within which the operator is able to teleoperate. Such volume must have adequate accuracy values for the teleoperation activity and at the same time consistent with the operator's ergonomics. Preferably, the volume also has a shape understandable to the operator in case it cannot be delimited by means of a display system or physical guides. In fact, for usability criteria it is important that the workspace is shaped so that the operator perceives the limits thereof.

In other words, the aforesaid "Operator Usable Workspace" is preferably selected so that it is:
  (i) understandable to the operator, thus referred to the console and not to the measuring system,
  (ii) reduced in size to avoid the regions of the "Master Measurable Workspace" which are not useful for ergonomics (this is particularly important in the case of magnetic systems which also permeate bodies, unlike optical tracking systems);
  (iii) reduced in size as a function of teleoperation quality criteria;
  (iv) reduced for regions where the master device must not be placed for reasons of operating field sterility.

Preferably, for the purposes of this patent, the term "master device workspace" is intended to indicate this "Operator Usable Workspace".
3. "Starting Workspace": this is the work volume within the "Operator Usable Workspace" where the master device is to be located at the time of entry into teleoperation. The reason for such a restriction with respect to the "Operator Usable Workspace" lies in the fact that starting near the edge, the operator could quickly exit the workspace. According to an implementation option, the "Starting Workspace" can be dynamically constructed based on the master-slave scale factor with "Starting Workspace".

The considerations regarding the spatial thresholds, which will be shown below, are applicable to the exit from the Operator Usable Workspace and the entry to the Starting Workspace.

Therefore, according to an implementation option, the system verifies that at the entry into teleoperation the master device is inside the "Starting Workspace", and that during teleoperation the master device does not exit the "Operator Usable Workspace".

The boundaries of the workspace can be variable depending on the contingent and specific conditions: for example, the workspace must exclude pockets specifically included for storing the master device even if they are close to the operator's position.

According to an implementation option, at the first entry into teleoperation, the position of each master device is independently fixed, and this results in a suitably scaled translation of the slave device, to avoid starting the teleoperation near an edge of the workspace.

Figure 3:
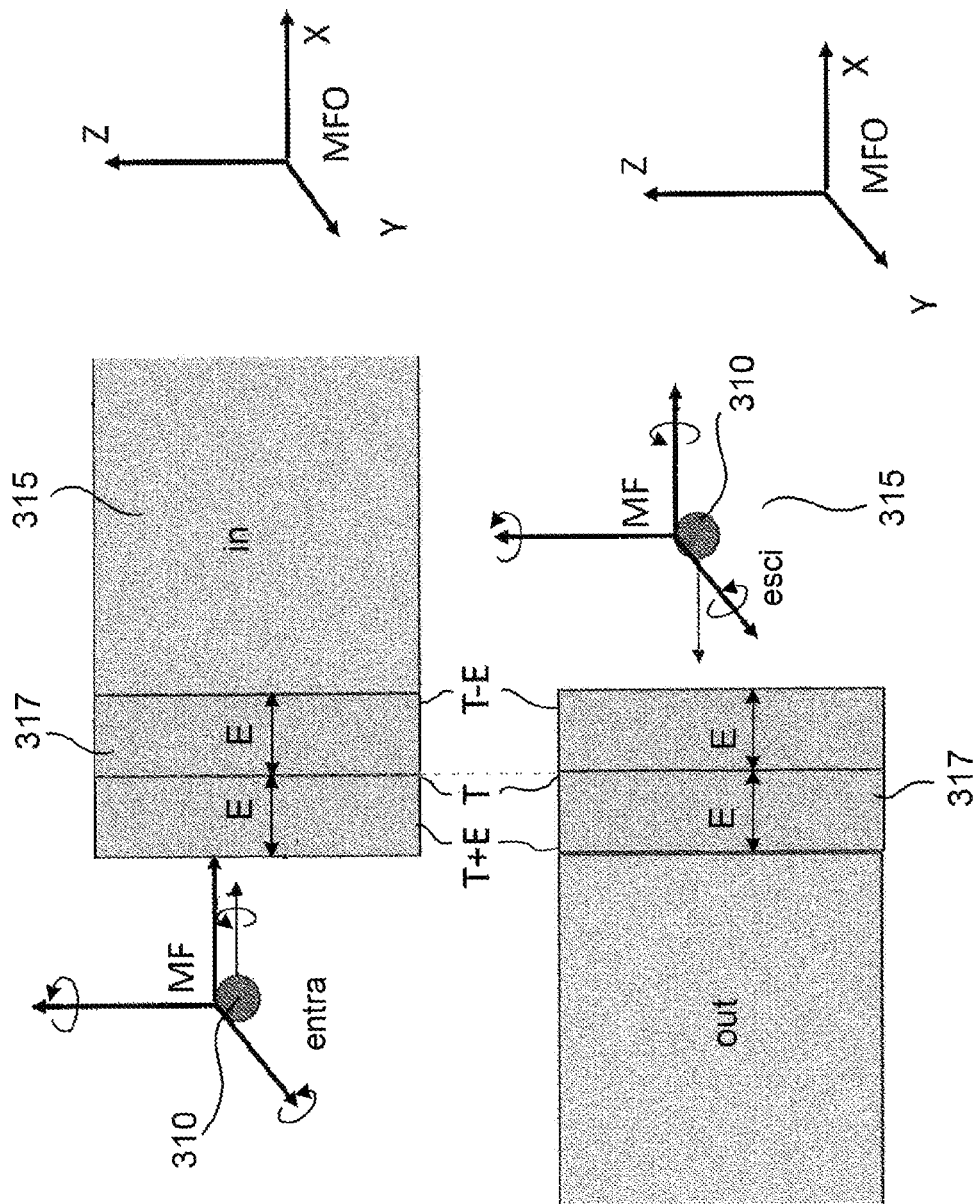
FIGS. 3(a) and 3(b) diagrammatically show input (a) and output (b) transitions from a master device workspace, provided in a method embodiment.

According to an example embodiment, shown for example in FIG. 3, if a spatial reference threshold T used for safety assessments entering and exiting workspace regions 315 delimited by the threshold T is defined, the measurement error must be taken into account in order to correctly evaluate the threshold and minimize oscillations.

Therefore, let Z be the measurement of a position X affected by maximum noise E, thus: $Z=X+-E$.

Let $X<T$ be defined within the threshold and $X>T$ outside the threshold.

Let the operator, i.e., the master device 310, in a situation outside the workspace region 315 ($X>>T$) and the stable entrance condition is to be estimated taking into account the margin of error as a function of the measurement Z.

Thus, by setting $Z<T-E$ it is observed that by replacing two cases we obtain the stable criterion that the operator is definitely within the workspace region 315. Any other larger value of Z does not meet the criterion of $X<T$.

$$X+E<T-E \text{ or } X<T-2E$$

$$X-E<T-E \text{ or } X<T$$

Again in accordance with this example, assuming that the operator, i.e., the master device 310, is within the workspace region 315 ($X<<T$) then $Z>T+E$ is the criterion sought for replacement $X>T$. By acting on the condition of Z with respect to T and E, it can be chosen to delay entry or exit according to usability or safety criteria.

If the inner edge ($T-E$) is always chosen, the safety is favored for the exit and usability is favored for the entry. FIG. 3 shows the master device 310 entering/exiting the edge region 317 from the workspace 315, in which the edge region 317 is defined by the threshold T taking into account the noise E.

Excessive Vibrations of the Master Device.

According to an embodiment, in which a further anomaly/fault associated with excessive vibrations of the master device is detected, the method comprises the following steps:
  detecting movements of the velocity vector above a certain threshold;
  detecting or counting the number or frequency of direction changes of the detected or calculated velocity vector of the master device;

comparing the aforesaid number or frequency of direction changes with a respective threshold value;

identifying the aforesaid anomaly/fault associated with excessive vibrations of the master device if the aforesaid number or frequency of counted or detected direction changes exceeds the aforesaid respective threshold value.

The counting of the number or frequency of changes of direction of the velocity vector occurs, for example, in a given period of time, for example 0.2 seconds. Thereby, since the band of the surgeon-robot system is typically 5 Hz, the system recognizes whether, through the master device, a 10 Hz motion command is provided as input. This feature seeks to identify such a situation as indicative of an anomaly, rather than removing it as would occur with the application of a step-by-step filter.

The monitoring of the master device velocity allows recognizing a sufficiently large number of oscillations in a predetermined time interval, for example identifying when the velocity reverses direction, and counting in a (floating or fixed) time window the number of oscillations which exceed a given amplitude above the predetermined threshold.

This functionality can be useful, particularly in the case of a magnetic tracking system, also for detecting any magnetic field disturbances due to an external magnetic field detected in the form of vibrations of the detected position signal of the master device.

The mono-directional case will be discussed in detail here. The velocity inversion of a continuous signal is obtainable as a minimum or maximum point of the derivative thereof over time. Given a single-axis position signal with fixed sampling dT (seconds), we can evaluate this point in various modes: (i) using polynomial filtering and fitting, (ii) voting on a floating window of length 2W+1.

In the case of "(i) fitting": perform the fitting of the position with an at least second order polynomial, and calculate if the acceleration is zero; then later they are estimated in the window given the velocities. In the case of "(ii) floating window": the local samples of instantaneous transformed velocity are inserted on three symbols (P Z N) corresponding to relative velocity values greater than a threshold V0, comprised in [−V0,V0] and less than −V0. The algorithm considers as an inversion point the first point that has LZ samples at zero velocity (at most, also 0) preceded by uniform sequences of non-negative values, followed by non-positive values, or the inverse.

A first implementation is based on pattern recognition with regular expression such as: [NZ]{L1,}[PZ]{L1,} or [PZ]{L1,}[NZ]{L1,}. The inversion point is the midpoint between the last and first symbol N,P in the first case and P,N in the second. It should be noted that it is not necessary to have a point where the velocity is zero.

In a second implementation, the sequence of P N is stored in a floating window which counts the number of contiguous occurrences of each P and N. A floating window of length W means at most W elements all 1 when there are alternations of P and N or 1 element if they are all P or N. Using the maximum scrolling algorithm on the sequence of such occurrences C1 . . . CK obtains the maximum point, and let it be Ci. Then, if Ci>=L1 and C(i−1)>=L1 or C(i+1)>=L1, an inversion point is obtained.

Preferably, if the measurement system, for any reason, does not provide a sample, the system resets and begins to fill the floating windows.

At this point, the system accumulates the inversion points over time. If the last two inversion points have a time distance greater than a predetermined threshold, the inversion count is reset. The distance between the two inversion points is then evaluated and if this is greater than a given threshold, the number of inversions is increased.

Extending the above to the three-dimensional case, a possible solution is to work by independent axes and have three distinct velocity direction change identifiers (one per axis).

Another embodiment with reference to the three-dimensional case is to work in a combined manner, as described below, with reference to what has already been discussed for the mono-dimensional case: the inversion point is then estimated based on the three-dimensional position, and the distance between vectors is used to estimate the amplitude of the oscillations.

In the case of estimation of the point by "(i) fitting", the same approach of the polynomial fitting set out above is applied, but extended to the three-dimensional case. The idea is to express the position with a polynomial, or sequence of polynomials (spline), then calculate the tangential relative velocity and finally use it as value Vr. One possible technique is B-Spline fitting. The problem is solvable with a least-squares optimization and controlled mainly by the number of desired control points. A preferred hypothesis is a continuous estimation of fitting based on filtering. Otherwise, the estimation of the inversion is based on the curvilinear representation of a three-dimensional trajectory going to decompose each new velocity vector with respect to the previous vector with tangential and normal motion components, as described below: given two points in time P1,P2 we define the velocity vector as V2=P2−P1. Given a third point P3 it is possible to evaluate what role the new velocity vector V3=P3−P2 has with respect to the previous component V3=v3t V3+V3N. The component v3t is a relative velocity and thus usable as Vr in the monoaxial solution.

For example, assume having a signal with natural oscillations up to 5 Hz, sampled at 100 Hz, with an accuracy of 0.1 mm.

Involuntary Opening of the Master Device.

According to an implementation option, the master device body comprises two rigid parts constrained in a joint, preferably an elastic joint, to at least rotate about a common axis defining a degree of freedom of opening/closing for the master device body, and the method comprises the step of calculating the opening angular velocity ω of two rigid parts of the master device body, based on the detected and/or calculated velocity vectors.

Therefore, according to this implementation option the method further comprises the steps of:

comparing the calculated opening angular velocity ω with a threshold angular velocity ω_thr, which can depend on the elastic rigidity of the elastic joint;

identifying the anomaly/fault condition associated with an involuntary opening of the master device if the aforesaid calculated opening angular velocity ω is greater than the aforesaid threshold angular velocity (ω_thr) according to the relation ω>ω_thr.

According to an implementation option, the threshold angular velocity value ω_thr belongs to the range between 0.15 and 0.50 rad/s.

According to similar implementation options, the aforesaid steps of calculating, comparing and identifying are performed not on the angular velocity, but on the angular acceleration, or on the linear acceleration, which can be obtained for example by monitoring the evolution over time of the velocity vector and/or the position vector.

According to another implementation option, referring to the case in which the master device consists of two rigid parts mutually connected in an elastic joint which tends to open such parts at least angularly when not pressed or held firmly in the user's hand, and the detectable anomaly is an involuntary opening of the master device, the method comprises the following steps:

- detecting the position vector and the respective evolution over time of each of the two detectable points;
- calculating the evolution over time of the distance between the aforesaid two detectable points, based on the evolution over time of the position vectors detected;
- calculating the opening linear velocity v of the master device, based on the evolution over time of the aforesaid distance;
- comparing the calculated opening linear velocity v with a threshold linear velocity v_thr;
- identifying the aforesaid anomaly/fault condition if v>v_thr.

The threshold velocity can be an approaching velocity threshold between the two rigid portions and/or a distancing velocity threshold.

For example, when in operating conditions and according to an embodiment which provides that the master device body has a linear degree of freedom of translation adapted to control an enslaved slave degree of freedom of opening/closing, a radial pressure action on the master device body determines the distancing of the two rigid parts, imparting a gripping action (opening/closing) to the surgical instrument.

Preferably, this implementation option which provides calculating the relative linear velocity of translation of the two rigid parts of the master device constrained to each other in translation allows identifying an anomaly/fault condition indicative of an uncontrolled behavior of the master device, like the implementation described above with reference to the involuntary opening in a master device having a rotational joint between the two rigid parts.

Thus, in summary, according to a method embodiment, by measuring or calculating the vector acceleration, i.e., in the modulus and linear or angular direction of the master device, at least the following information is obtained:

- master device drop: if the acceleration is equal to g and directed downwards, then the robotic system is immediately stopped, to prevent the slave from also heading downwards, and therefore, presumably, towards the patient;
- the master device has an excessive acceleration (e.g., equal to or greater than 3 g) in any direction; also in this case, the robotic system is immediately stopped;
- unintentional opening of the master device: if the relative acceleration of two points of the master device is greater than the elastic return acceleration between the aforesaid two points (between which there is a joint, and a spring adapted to open the joint).

The vector acceleration of the master device is either directly detected by one or more accelerometers, or derived from monitoring the evolution of the position vector, in turn detected.

As disclosed above, the present method relates to a broad class of master device interfaces for robotic systems of surgical teleoperation, characterized by position and orientation measurements.

In particular, master devices with two parts, or tips, which can be closed with a hinge or hinge joint are for example considered. Each part is associated with a position measurement, which is directly measured or deducted.

For the control of the slave device, and in particular of the micro-surgical instrument (or "end-effector") associated therewith, a master reference coordinate frame (or "Master Frame") and a respective point of origin (or "Master Frame Origin" MFO) can be defined.

The position of one or more reference points of the master device, at any time, is thus defined with respect to the coordinates of the aforesaid master reference coordinate frame, with respect to the origin (MFO) of such a coordinate frame.

As already noted, in some embodiments, the master reference coordinate frame, and the related position of the master device, is measured directly, for example using an optical marker placed on the master device, at an appropriately chosen point. In this case, the gripping angle of the master device is measured with another technique, for example a magnetic encoder.

In other embodiments, where the master device is always "gripped", with two parts hinged in a joint, the method includes measuring the position of each of the aforesaid two parts (or of the respective tips) of the master device. In such a case, each of the two parts of the master device is associated with a frame of reference coordinates thereof (indicated here respectively as MF #1 and MF #2), expressed with respect to the origin of the aforesaid General Master Frame (MFO).

The coordinate transformations between the general Master Frame (with origin MFO) and the Master Frames of the parts of the master device, MF #1 and MF #2, can be expressed by known coordinate transformation techniques, for example as the average between the two Master Frames MF #1 and MF #2, by averaging the position and orientations.

In such a case, the measurements performed on the two parts of the master device can provide up to 12 degrees of freedom detected: 3 position coordinates and 3 orientation values for the first master device portion; 3 position coordinates and 3 orientation values for the second master device portion.

Such detections always allow (and also with redundancy) detecting the 7 degrees of freedom of the mechanical structure of the master device.

With respect to the coordinate frames shown in the figures and used in the method, it should be noted that the reference frame denoted as MFO is a general reference frame (or "Master Frame" or "Master Frame Origin") for the master device (e.g., associated with the master device workspace); the reference frames denoted as MF #1 and MF #2 (FIG. 1) are local reference frames (or "Master Frame") which are integral with the two parts of the master device; the reference frames MFM (in FIG. 1), MF1 and MF2 (FIGS. 4, 4bis and 6ter) are local reference frames which are integral with a master device (e.g., associated with a virtual midpoint between the points where two sensors being integral with the master device are located); the reference frame SFO (in FIG. 4bis) is a general reference frame (or "Slave Frame Origin") for the slave device (e.g., associated with a workspace of the slave device).

Figures 7, 8:
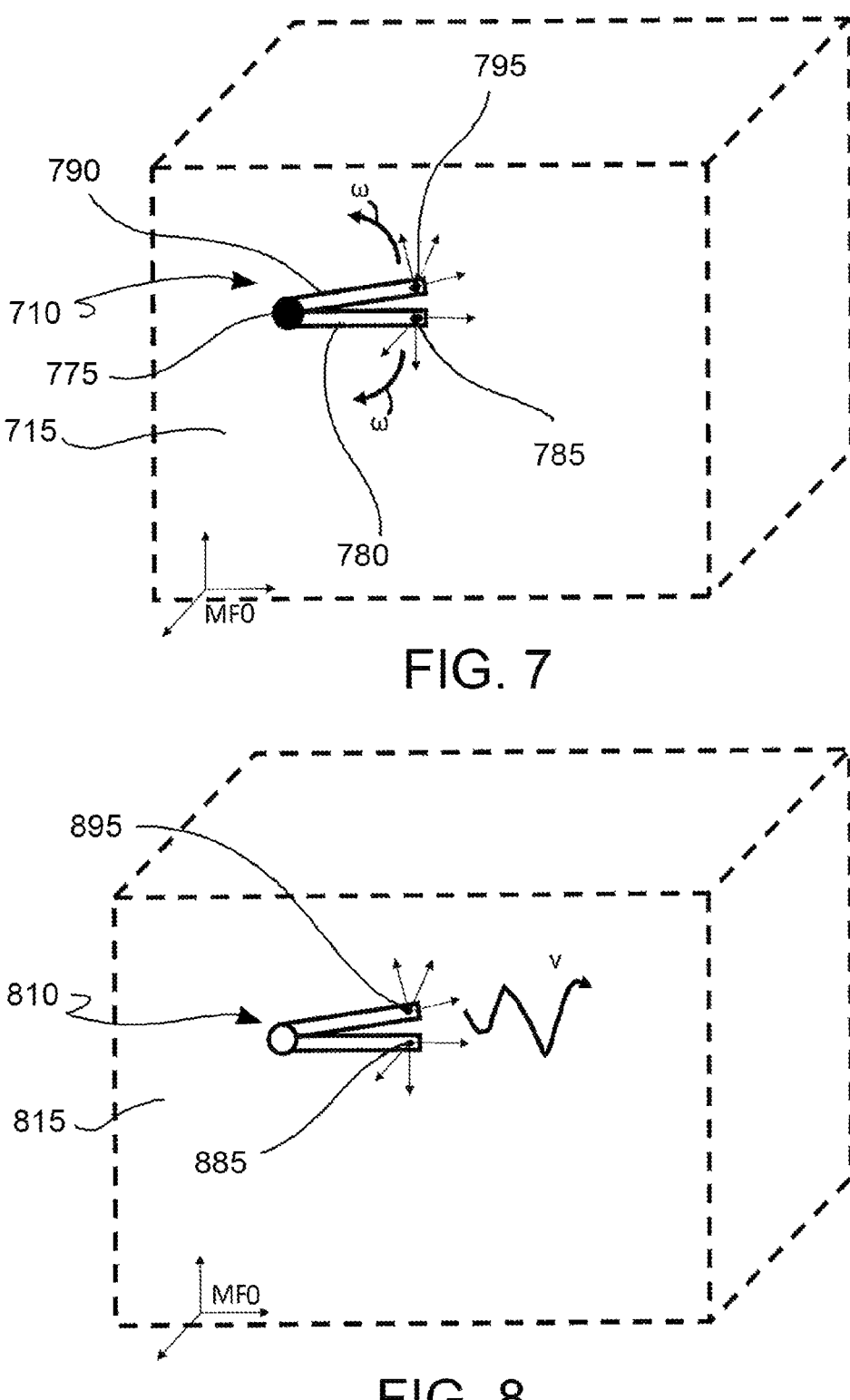
FIGS. 7 and 8 diagrammatically show some anomalies that are detectable based on the velocity of the master device, according to some embodiments of the present method.

The examples shown in FIGS. 1, 2 and 7 refer to a "gripper" type master device which involves the application of a force of the fingers of the gripping hand approximately in the middle between the hinge joint and the tips of the two arms of the gripper (corresponding to the "two parts" of the master device mentioned several times). This type of master device is characterized by a total of 7 degrees of freedom: three orientation degrees of freedom, three position degrees of freedom and the opening between the gripper arms. As already shown, optical or magnetic technologies can be used to detect the position of the gripper arms.

FIGS. 1 and 2 depict the master device 110 with the two sensors S1, S2 arranged near the tips of the arms 180, 190 of the gripper formed by the master device 110.

In FIG. 1, the hinge joint OJ is on the left, and allows a rotation of the arms with an axis parallel to the two axes z1 and z2 of the two arms. The axes x1 and x2 are in the direction of the arms, with a direction away from the joint.

The position and rotation measurements of each of the two sensors can be represented by a three-dimensional vector of the position (thus obtaining two vectors which we indicate as p1 and p2) and by a rotation matrix for each arm (thus obtaining two rotation matrices which we indicate as R1 and R2). Each sensor is then associated with respective position and rotation information, (p1, R1) and (p2, R2).

It should be noted that the rotation can be associated with the three-dimensional orthogonal subgroup SO(3) and thus the number of degrees of freedom is always 3 (regardless of the type of depiction, whether it is based on a rotation matrix with 9 numbers, as exemplified herein, or based on 3 Euler angles (3), or based on quaternions).

The arrangement (i.e., position and rotation) of the reference points (or tips) of the arms allows calculating an arrangement (i.e., position and rotation) of the entire master device, for example with a position calculated as the average pM of the two positions p1 and p2, and rotation as an average of the rotations (i.e., a matrix RM having as elements the averages of the respective elements of R1 and R2). The opening angle α of the gripper can be calculated using the distances between the tips and the known lengths of the master device arms, i.e., the known distances between the joint and each of the reference points provided with sensors (assuming that the sensors S1, S2 are placed at equidistant points from the joint OJ, the aforesaid two distances are equal).

In the example shown in FIG. 3(*a*), an unconstrained master device 310 is diagrammatically shown during a transition entering a master workspace 315, in which an edge band 317 is defined around the limit T of the workspace 315; for example, the edge band 317 can be determined by an error or noise E which derives from the detection quality of the master device 310 by the tracking system, and therefore the edge band 317 is delimited by the positions T+E and T−E.

In the example shown in FIG. 3(*b*), an unconstrained master device 310 is diagrammatically shown during a transition exiting a master workspace 315, in which an edge band 317 is defined around the limit T of the workspace 315; for example, the edge band 317 can be determined by an error or noise E which derives from the detection quality of the master device 310 by the tracking system, and therefore the edge band 317 is delimited by the positions T−E and T+E.

Figure 4:
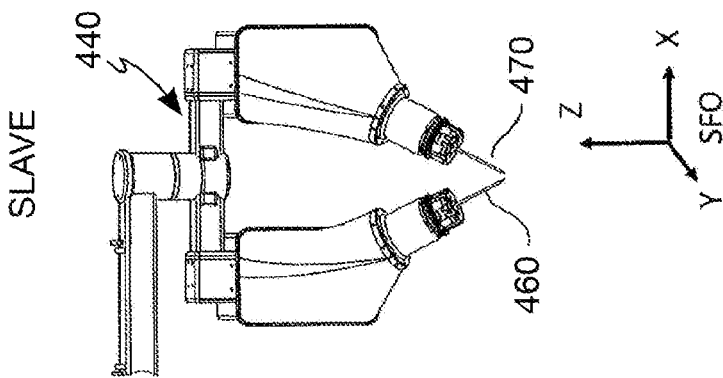
FIG. 4 diagrammatically shows an embodiment of a teleoperated system, according to the present invention, to which at least one master device workspace is associated.
Figure 4:
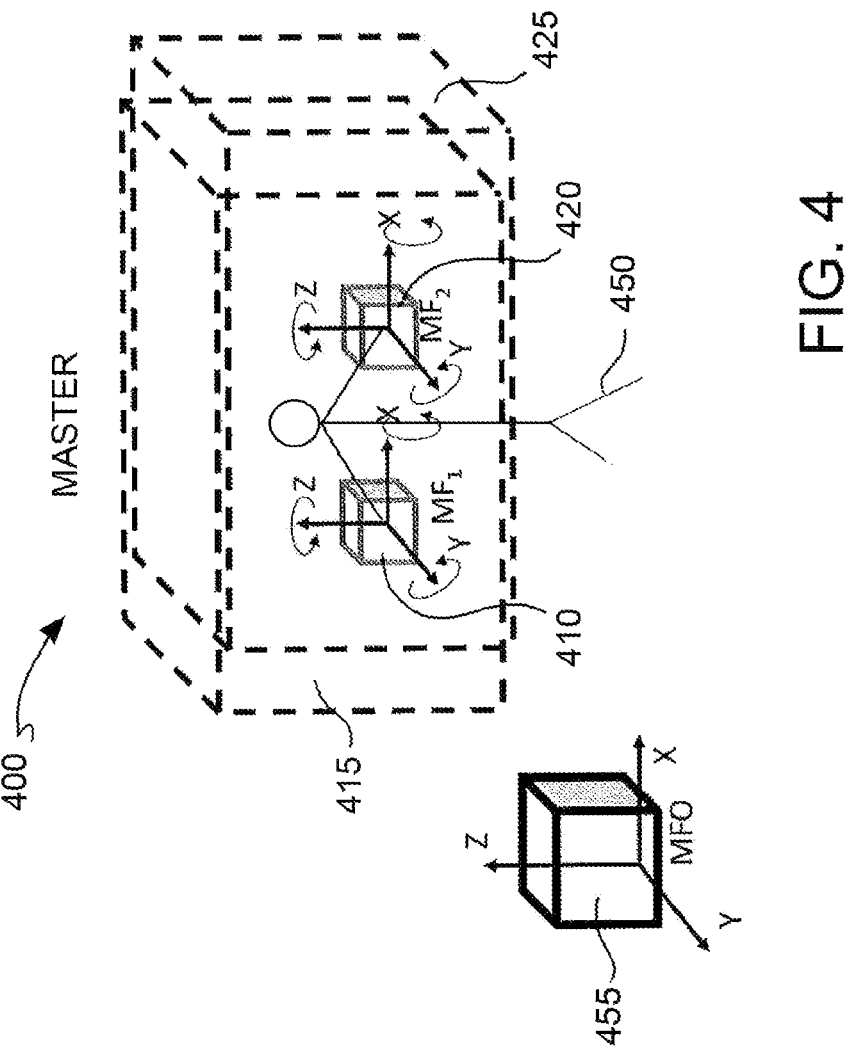

According to an embodiment shown in FIG. 4, a robotic teleoperated surgery system 400 comprises at least one unconstrained master device 410, 420 having an assigned workspace 415, 425 (in the illustrated example, two diagrammatically shown unconstrained master devices 410, 420 are diagrammatically shown held in hand by a surgeon 450), a control unit which is integral with the console 455, and a slave device 440 (in the illustrated example two slave surgical instruments 460, 470 are shown).

According to an embodiment shown in FIG. 4bis, a robotic teleoperated surgery system 400 comprises at least one unconstrained master device having an assigned workspace 415 (in the illustrated example two diagrammatically shown unconstrained master devices 410, 420 are diagrammatically shown held in hand by a surgeon 450), a console

455 which is integral with the reference frame MFO and preferably comprising a control unit, and a slave device 440 (in the illustrated example two slave surgical instruments 460, 470 are shown).

FIG. 5 diagrammatically shows an unconstrained master device 510 within a workspace 515 assigned thereto, in which a teleoperation start space region 516 is shown, herein entirely contained in the workspace 515, and where, in this illustrated example, the master device 510 is provided with a pair of identifying sensors or markers 585, 595; for example, only when the master device 510 is within the teleoperation start space region 516 the system is configured to enable the start of the teleoperation.

According to an embodiment shown for example in FIG. 5bis, the reference frame MFO is integral with a console comprising a chair 554 (in the illustrated example the reference frame MFO is integral with a portion of the chair 554). For example, a tracking source is placed to be integral with a portion of the chair 554 defining a work volume 515, and in which a teleoperation start space region 516 is shown herein entirely contained in the workspace 515; for example, only when the master device 510 is within the teleoperation start space region 516 is the system configured to enable the start of the teleoperation.

According to an embodiment shown for example in FIG. 5ter, the reference frame MFO is integral with a master console 555 defining a work volume 515 being integral with the master console 555; in the illustrated example, two unconstrained master devices 510, 520 held in hand by a surgeon 550 and wired by data link 511, 512 to the console 555 are diagrammatically shown; in the example shown, the console 555 comprises a screen 557 for displaying the operating field and/or system and/or operating field status parameters.

Figure 6:
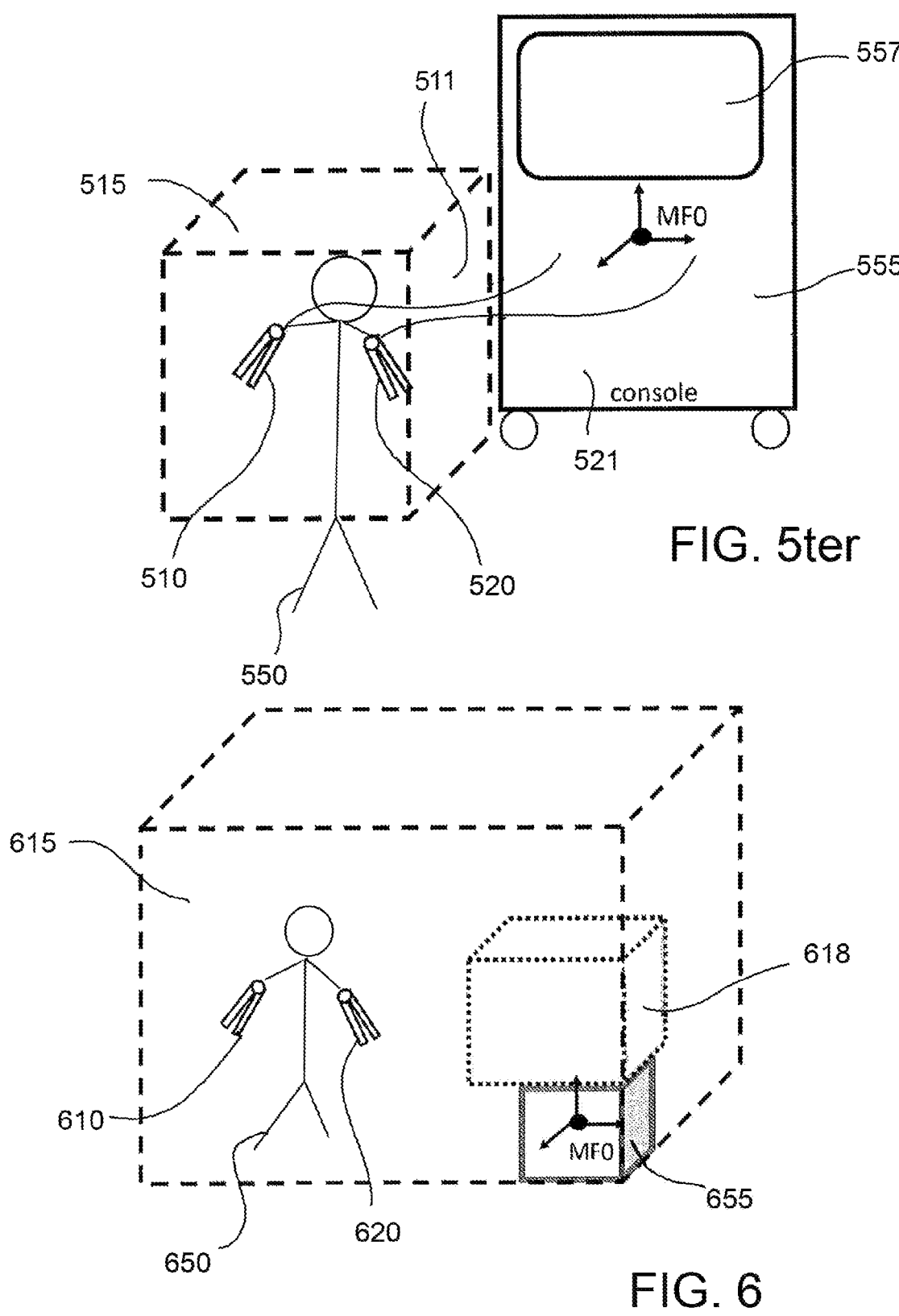

According to an embodiment shown for example in FIG. 6, there are two volumes 615, 618 which are integral with the console 655 comprising a work volume 615 and a stowage or resting volume 618, in which when the master device 615, 625 is within the stowage volume 618, the system does not enable an entry into a teleoperation state. For example, the stowage volume 618 can be positioned at or near the console 655 and/or at or within elements intended to store the master device 610, 620 when not in use.

According to an embodiment shown for example in FIG. 6bis, two work volumes 615, 625 which are integral with the console 655 are defined, comprising a left work volume 615 and a right work volume 625, and in which preferably the system enables an entry into a teleoperation state if the left master device 610 is within the left work volume 615 and the right master device 620 is within the right work volume 625.

According to an embodiment shown for example in FIG. 6ter, the system enables an entry into a teleoperation state if the left master device 610 and the right master device 620 are both within the work volume 615, and if the left master device 610 is to the left of the right master device 625.

FIGS. 7 and 8 show some anomalies/faults which can be identified based on velocity information of at least one point of the unconstrained master device 710, 810 within a workspace 715, 815 assigned thereto.

In the example shown in FIG. 7, the monitoring of the angular velocity ω of two points of the master device 710, said two points being respectively identifiers of the rigid parts 780, 790 constrained in a joint 775 to rotate about a common axis, allows detecting an involuntary opening of the master device (in the example shown here, the master device 710 is provided with an identifying sensor or marker 785, 795 on each of the two rigid parts 780, 790).

In replacement or in addition, the velocity monitoring can be a monitoring of the linear velocity of two points of the master device.

In the example shown in FIG. 8, the velocity monitoring allows excessive vibrations of the master device to be detected (in the example shown herein, the master device 810 is provided with a pair of identifying sensors or markers 885, 895) based, for example, on monitoring the direction of the velocity v and/or counting the direction changes of the velocity vector v detected within the work volume 815.

According to an embodiment shown for example in FIG. 9, there are three volumes 915, 919, 914 which are integral with the console comprising: a work volume 915 in which when the master device 910 is located therein, the system enables teleoperation (for example commands a slave surgical instrument 960), a suspended teleoperation volume 919 in which when the master device 910 is located therein and simultaneously outside the work volume 915 the system suspends teleoperation, and a tracking volume 914 representing the detection limit in which when the master device 910 is located therein and simultaneously outside the suspended teleoperation volume 919 the system excludes teleoperation (i.e., the master device 910 is out of teleoperation).

According to an embodiment shown for example in FIG. 9bis, there are three volumes 915, 919, 914 which are integral with the console comprising: a work volume 915 delimited by the limit threshold or surface T in which, when the master device 910 is located therein, the system enables teleoperation (for example commands a slave surgical instrument 960), a suspended teleoperation volume 919 delimited by the limit threshold or surface T' in which when the master device 910 is located therein and simultaneously outside the work volume 915 the system suspends teleoperation, and a tracking volume 914 delimited by the limit threshold or surface T" representing the detection limit in which when the master device 910 is located therein and simultaneously outside the suspended teleoperation volume 919 the system excludes teleoperation (i.e., the master device 910 is out of teleoperation). The limit thresholds or surfaces T, T' and T" can be subject to the measurement or noise error E mentioned above with reference to FIG. 3 (a)-(b).

Figure 10:
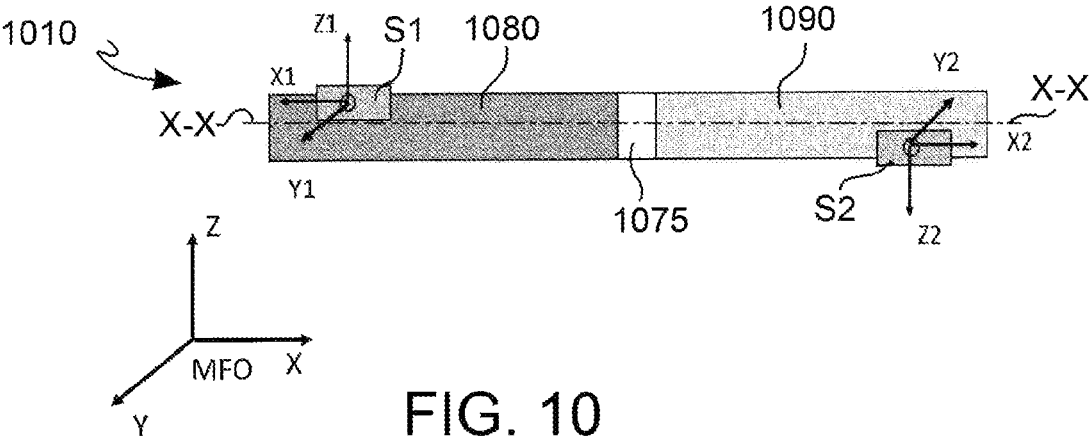
FIG. 10 diagrammatically shows an embodiment of the master device.

The embodiment diagrammatically shown in FIG. 10 shows an unconstrained master device 1010 comprising two parts 1080, 1090 constrained in a joint 1075 to relatively translate along a common axis X-X, in which for example the two parts 1080, 1090 are constrained co-linear to each other, in which sensors S1, S2 are placed to be integral with each of the two parts 1080, 1090. According to an implementation option, monitoring the linear or angular velocity of each sensor S1, S2 allows detecting an anomaly/fault condition. For example, by pressing on the joint 1075, which is preferably an elastic joint, the two parts 1080, 1090 move away, and in case of loss of control of the master device 1010 by the surgeon the two parts 1080, 1090 relatively approach, and in which the monitoring of the relative approaching velocity allows detecting an anomaly condition, for example if the relative approaching velocity is greater than a velocity threshold. In accordance with an implementation option, the system monitors the angular velocity of at least one sensor S1, S2 to detect and recognize an anomaly/fault condition such as excessive vibrations.

As can be seen, the objects of the present invention as previously indicated are fully achieved by the method described above by virtue of the features disclosed above in detail.

In fact, the method and system described allow an effective and real-time verification of detecting several possible operating anomalies/faults of the master device, or possible abnormal situation of the master device, and recognizing the type of anomaly.

Thus, it is possible to satisfy the need to apply procedures for verifying any abnormal operating conditions of the master device in real time, conducted automatically by the robot control system for medical or surgical teleoperation, which are such as to be efficient and reliable, in order to meet the stringent safety requirements which are required by such applications.

This is obtained by detecting at least one position vector of at least one point associable with the master and comparing the one or more detected quantities with one or more respective predeterminable threshold values.

Once a structural or functional anomaly/fault of the master device has been identified, the teleoperation can be immediately and promptly interrupted, thus avoiding that such an anomaly/fault is reflected in a consequent anomaly/fault in the operation of the slave device and the surgical instrument associated therewith, intended to act on the patient, with possible even serious consequences on the patient himself.

Thereby, the objective of improving patient safety is achieved, meeting the very strict safety requirements which must be respected in the operating environment considered.

In order to meet contingent needs, those skilled in the art may make changes and adaptations to the embodiments of the method described above or can replace elements with others which are functionally equivalent, without departing from the scope of the following claims. All the features described above as belonging to a possible embodiment may be implemented irrespective of the other embodiments described.

The invention claimed is:

1. A method for identifying and recognizing and/or discriminating at least one anomaly condition in using a master device, which is hand-held, adapted to be held in hand by an operator, to control a robotic system for medical or surgical teleoperation, the master device being mechanically unconstrained relative to said robotic system; wherein the method comprises:

detecting, by one or more sensors, a position vector of at least one point belonging to or integral with the master device, or of a virtual point uniquely and rigidly associated with the master device;

identifying and recognizing and/or discriminating at least one detectable anomaly based on said at least one detected position vector, or based on at least one component of the at least one detected position vector, wherein said at least one detectable anomaly comprises at least an incorrect positioning of the master device with respect to a predetermined workspace of the master device, and wherein each of said at least one detectable anomaly is associated with at least one system state change to be performed if the at least one detectable anomaly is detected, said at least one state change comprising exit from a teleoperation state, wherein a suspended teleoperation volume is defined, which extends around the master device workspace and is larger than the master device workspace, said suspended teleoperation volume being a volume in which the robotic system provides for a suspended teleoperation, wherein the suspended teleoperation is a limited teleoperation which prevents at least translation movements of a control point of a slave device, or which limits rotational movements of the control point of the slave device, or which prevents all movements of the control point of the slave device, wherein the method comprises the further step of:

switching from the teleoperation state to a suspended teleoperation state when the master device exits the workspace limits and enters the suspended teleoperation volume.

2. A method according to claim 1, wherein the robotic system for medical or surgical teleoperation comprises:

said master device adapted to be held in hand by a surgeon during surgery, and configured to detect a manual command of the surgeon and generate a respective first electrical command signal;

at least one slave robotic assembly, comprising at least one slave surgical instrument configured to operate on a patient, in a manner controlled by the master device, so that movement of the master device results in a respective movement, desired and controlled, of the slave device;

a control unit provided with a computer, configured to receive said first electrical command signal from the master device, generate a second electrical command signal, based on the first electrical command signal, and provide the second electrical command signal to the slave robotic assembly, to actuate the at least one slave surgical instrument;

wherein said control unit is operatively connected to said one or more sensors to receive at least a third electrical signal, or to receive said first electrical signal, representative of said detected position vector and/or of the related evolution over time, and wherein said step of identifying and recognizing and/or discriminating at least one detectable anomaly is performed by said control unit.

3. A method according to claim 1, wherein the at least one detectable anomaly comprises detecting a prohibited positioning of the master device outside predetermined spatial limits as permitted, and wherein the method comprises:

comparing the detected position of said at least one point belonging to or integral with the master device, or virtual point uniquely and rigidly associated with the master device, with a predetermined limit surface, representative of said predetermined spatial limits;

identifying said prohibited positioning anomaly of the master device if said detected position is outside said predetermined limit surface, wherein said position of the at least one point belonging to or integral with the master device, or virtual point uniquely and rigidly associated with the master device, and said predetermined limit surface are defined with respect to a reference coordinate frame associated with the robotic system for teleoperated surgery, and having predetermined axes and origin in a predetermined point.

4. A method according to claim 3, wherein the robotic system for medical or surgical teleoperation comprises an operating console, wherein said reference coordinate frame is integral with said robotic system console, wherein, the operating console comprises at least one surgical chair comprising at least one seating surface for the surgeon to sit thereon during surgery, wherein said reference coordinate frame is integral with said at least one surgical chair, and with said at least one seating surface.

5. A method according to claim 3, wherein said permitted spatial limits are defined as a sphere-shaped workspace or volume, and said predetermined limit surface is the spherical surface of said sphere, or wherein said permitted spatial limits are defined as a box-shaped or parallelepiped-shaped workspace or volume, and said predetermined limit surface is a surface of said box or parallelepiped.

6. A method according to claim 5, wherein the robotic system for medical or surgical teleoperation further comprises at least one tracking system, for detecting an input position and orientation of the master device within a predetermined tracking volume, so that actuation of the slave surgical instrument depends on the manual command given by a surgeon by the master device and/or on a position and orientation of the master device, wherein said master device workspace is contained in said tracking volume, or said master device workspace is a subset of the tracking volume, or wherein a teleoperation start space is predetermined, which is contained in the master device workspace, or said teleoperation start space is a subset of the master device workspace, wherein the method includes the step of:

allowing start of the teleoperation, or start of a step of preparatory checks, only if the detected position of the master device is located within said teleoperation start space.

7. A method according to claim 1, wherein the master device is a hand-held master device, comprising two rigid constrained to relatively rotate or translate with respect to a common axis, wherein said detecting step comprises detecting, by respective sensors, the position vector and/or position vector evolution over time of at least two detectable points, a first point belonging to or integral with one of said rigid parts of the master device and a second point belonging to or integral with the other one of said rigid parts of the device.

8. A method according to claim 7, wherein said step of detecting at least one position vector comprises detecting the position vector of said at least two detectable points, and/or the position vector of at least one of the following further points:

midpoint between said two detected points and/or the center of gravity of the master device, and/or a rotational joint of the master device, and/or a prismatic joint of the master device, and/or wherein the master device body comprises two free tips or ends, a first free tip or end belonging to or integral with one of said rigid parts of the master device and a second free tip or end belonging to or integral with the other of said rigid parts of the device, and wherein said two detectable points correspond to and/or are associated with said two free tips or ends of the master device, respectively.

9. A method according to claim 1, wherein when the master device is determined to be outside permitted spatial limits, said system state change is an immediate exit of the robotic system from the teleoperation state, or an immediate suspension of the teleoperation state.

10. A method according to claim 9, wherein when the master device and/or the slave device are determined to be within a proximity threshold, within said spatial limit and/or orientation limits, the method includes the further step of:

communicating to the operator, by an acoustic and/or visual communication signal, a condition of proximity of the master device and/or the slave device to the permitted spatial limits, in order to allow the operator to act to avoid exiting the spatial limits and exiting the teleoperation, wherein said communication signal is an acoustic signal, and wherein said acoustic signal increases frequency of the communication signal as a distance of the master device or of the slave device from the spatial limit decreases, in an interval between the proximity threshold and a surface corresponding to the spatial limit, or wherein said communication signal is a visual signal, and wherein frequency of the communication of the visual signal increases as the distance of the master device or of the slave device from the spatial limit decreases, in the interval between the proximity threshold and the surface corresponding to the spatial limit.

11. A method according to claim 9, wherein the method further comprises:

allowing restart of the teleoperation of the robotic system when, in real time, the master device being returned to the permitted spatial limits is detected, or inhibiting the restart of the teleoperation of the robotic system even if, in real time, the master device being returned to the permitted spatial limits is detected, and restarting procedures for preparation and start of teleoperation and/or preliminary realignment operations, wherein said permitted spatial limits are defined by said master device workspace or by a teleoperation start space.

12. A method according to claim 1, wherein, when the master device exits the limits of said suspended teleoperation volume, the robotic system immediately exits the teleoperation step, and/or wherein entry or exit into/from the suspended teleoperation volume is indicated to the operator by a respective acoustic and/or visual and/or tactile signal, and/or wherein the method further comprises:

permitting the robotic system to return to the teleoperation state, with restart of teleoperation, when the master device being returned from the suspended teleoperation volume to the workspace limits is detected, and/or wherein, at an end of a suspended teleoperation step, and before starting teleoperation, the method includes a step of alignment with motion, in which the slave device moves to reach a position and orientation corresponding to actual and current position and orientation of the master device, and/or wherein, during said step of alignment with motion, the slave device is only permitted to vary control point orientation, or the slave device is permitted to move according to degrees of freedom of orientation and grip, and/or wherein the entry into the step of alignment with motion is permitted only if at least some verification checks are passed, said verification checks comprising at least the following checks: misalignment in master-slave orientation below a certain threshold, and/or orientation pose of the master being reachable within the slave workspace.

13. A method according to claim 1, wherein, if movements of the master device and the slave device are scaled by a scale factor, said master device workspace and/or teleoperation start space and/or suspended teleoperation volume grow with the scale factor.

14. A method according to claim 1, wherein the robotic system comprises two master devices, and wherein the method comprises exiting the teleoperation and/or suspending the teleoperation of both master devices if even only one of the master devices exits permitted spatial limits.

15. A method according to claim 1, comprising the further step of:

verifying that the slave device is within a permitted slave device workspace;

if the slave device is verified to be outside the permitted slave device workspace, notifying the user that a slave device positioning anomaly has emerged, and immediately stopping the teleoperation by the robotic system, wherein the slave device workspace comprises a spatial set of all positions which are reachable from a control point of the slave device as a consequence of possible poses and/or orientations of an articulated surgical instrument of the slave device.

16. A method according to claim 1, comprising the further step of calculating linear velocity and/or angular velocity and/or linear acceleration and/or angular acceleration of said at least one point belonging to or integral with the master device, or a virtual point associated uniquely and rigidly with the master device, based on evolution over time of the respective position vector detected, and comprising detecting said at least one detectable anomaly or detecting one or more further anomalies based on said linear velocity and/or angular velocity and/or linear acceleration and/or angular acceleration calculated.

17. A method for managing anomalies identified in a master device of a master-slave robotic system for surgical or medical teleoperation, the master device being hand-held, and adapted to be held in hand by an operator, to control a robotic system for medical or surgical teleoperation, the master device being mechanically unconstrained relative to said robotic system; the method comprising the steps of:

detecting, by one or more sensors, a position vector of at least one point belonging to or integral with the master device, or of a virtual point uniquely and rigidly associated with the master device;

identifying and recognizing and/or discriminating at least one detectable anomaly based on said at least one detected position vector, or based on at least one component of the at least one detected position vector, wherein said at least one detectable anomaly comprises at least an incorrect positioning of the master device with respect to a predetermined workspace of the master device, wherein each of said at least one detectable anomaly is associated with at least one system state change to be performed if the at least one detectable anomaly is detected, said at least one state change comprising exit from a teleoperation state, wherein a suspended teleoperation volume is defined, which extends around the master device workspace and is larger than the master device workspace, said suspended teleoperation volume being a volume in which the robotic system provides for a suspended teleoperation, wherein the suspended teleoperation is a limited teleoperation which prevents at least translation movements of a control point of a slave device, or which limits rotational movements of the control point of the slave device, or which prevents all movements of the control point of the slave device, the method comprising the further step of:

switching from the teleoperation state to a suspended teleoperation state when the master device exits the workspace limits and enters the suspended teleoperation volume, if at least any one of said at least one anomaly condition is determined, immediately stopping or suspending the teleoperation and movements of a surgical instrument of the slave device.

18. A robotic system for medical or surgical teleoperation comprising:

a master device, adapted to be held in hand by a surgeon during surgery, and configured to detect a manual command of the surgeon and generate a respective first electrical command signal;

at least one slave device, or slave robotic assembly, comprising at least one slave surgical instrument configured to operate on a patient, in a manner controlled by the master device;

a control unit provided with a computer, configured to receive said first electrical command signal from the master device, generate a second electrical command signal, based on the first electrical command signal, and provide the second electrical command signal to the slave robotic assembly, to actuate the at least one slave surgical instrument;

wherein said control unit is configured to:

detect, by one or more sensors with which the control unit is operatively connected, a position vector of at least one point belonging to or integral with the master device, or of a virtual point uniquely and rigidly associated with the master device;

identifying and recognizing and/or discriminating at least one detectable anomaly based on said at least one detected position vector, or based on at least one component of the at least one detected position vector, wherein said at least one detectable anomaly comprise at least an incorrect positioning of the master device with respect to a predetermined of the master device, and wherein each of said at least one detectable anomaly is associated with at least one system state change to be performed if the at least one detectable anomaly is detected, said at least one state change comprising exit from a teleoperation state, wherein a suspended teleoperation volume is defined, which extends around a master device workspace and is larger than the master device workspace, said suspended teleoperation volume being a volume in which the robotic system provides for a suspended teleoperation, wherein the suspended teleoperation is a limited teleoperation which prevents at least translation movements of a control point of a slave device, or which limits rotational movements of the control point of the slave device, or which prevents all movements of the control point of the slave device, wherein the control unit of the robotic system is further configured to cause switching from the teleoperation state to a suspended teleoperation state when the master device exits limits of the workspace and enters the suspended teleoperation volume.

* * * * *